(12) United States Patent
Troxler

(10) Patent No.: US 8,299,808 B2
(45) Date of Patent: Oct. 30, 2012

(54) APPARATUSES AND SYSTEMS FOR DENSITY GAUGE CALIBRATION AND REFERENCE EMULATION

(75) Inventor: Robert Ernest Troxler, Raleigh, NC (US)

(73) Assignee: Troxler Electronic Laboratories Inc., Research Triangle Park, NC (US)

( * ) Notice: Subject to any disclaimer, the term of this patent is extended or adjusted under 35 U.S.C. 154(b) by 198 days.

(21) Appl. No.: 12/799,495

(22) Filed: Apr. 26, 2010

(65) Prior Publication Data

US 2011/0260736 A1    Oct. 27, 2011

Related U.S. Application Data

(63) Continuation of application No. 11/384,005, filed on Mar. 17, 2006, now Pat. No. 7,705,614.

(60) Provisional application No. 60/663,420, filed on Mar. 18, 2005.

(51) Int. Cl.
 *G01R 27/26*    (2006.01)

(52) U.S. Cl. .................... 324/663; 324/689

(58) Field of Classification Search .............. 324/663, 324/658, 649, 600, 634, 640, 643, 664; 73/73, 73/74, 1.01; 702/127, 137; 703/23, 28; 714/28
See application file for complete search history.

(56) References Cited

U.S. PATENT DOCUMENTS

| | | | | |
|---|---|---|---|---|
| 4,147,976 A | * | 4/1979 | Wang | 324/689 |
| 4,924,173 A | * | 5/1990 | Dishman | 324/690 |
| 5,835,505 A | * | 11/1998 | Nishimichi et al. | 714/724 |
| 6,446,033 B1 | * | 9/2002 | Tatsumi | 703/14 |
| 2002/0039028 A1 | * | 4/2002 | Douglas et al. | 324/658 |
| 2002/0190728 A1 | * | 12/2002 | Gandrud | 324/663 |
| 2006/0065971 A1 | * | 3/2006 | Powell et al. | 257/704 |
| 2006/0205204 A1 | * | 9/2006 | Beck | 438/628 |

* cited by examiner

*Primary Examiner* — Hoai-An D Nguyen

(57) ABSTRACT

Apparatuses and systems for emulating electrical characteristics of a material having a known dielectric response are disclosed for standardizing and calibrating of electromagnetic devices. The emulator apparatus can include an electrically non-conductive layer having a dielectric constant less than the material dielectric constant and an electrically conductive layer adjacent the non-conductive layer. Artificial dielectrics for emulating the dielectric response of a material are also disclosed including a substrate matrix having a dielectric constant less than the material dielectric constant and an additive combined with the substrate, the additive having a dielectric constant higher than the material dielectric constant.

14 Claims, 15 Drawing Sheets

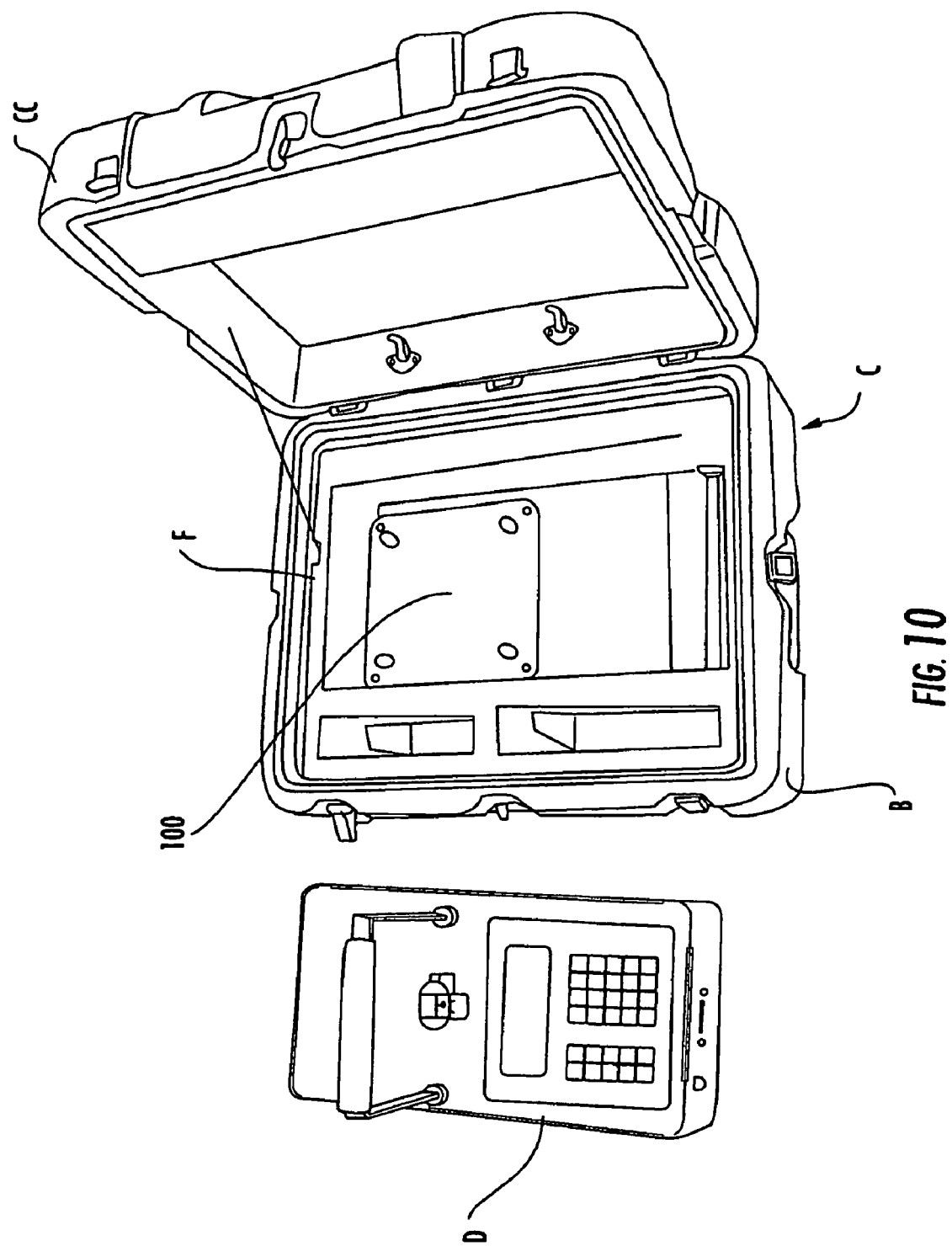

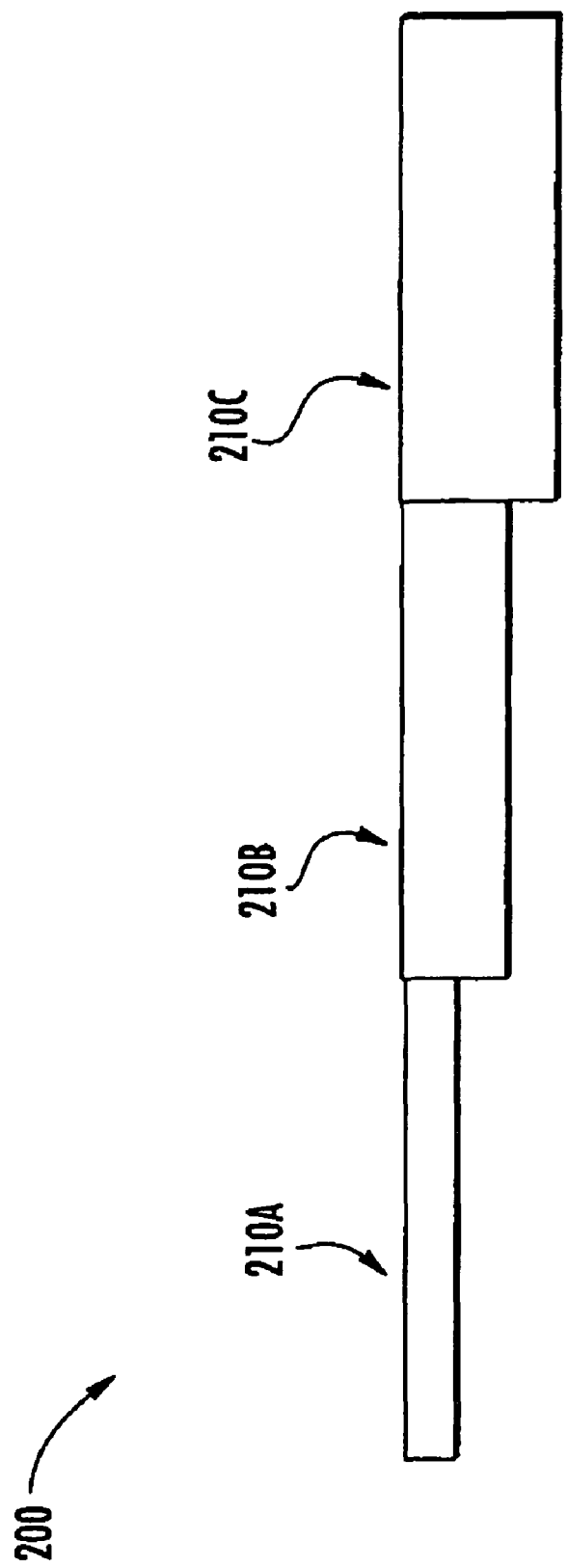

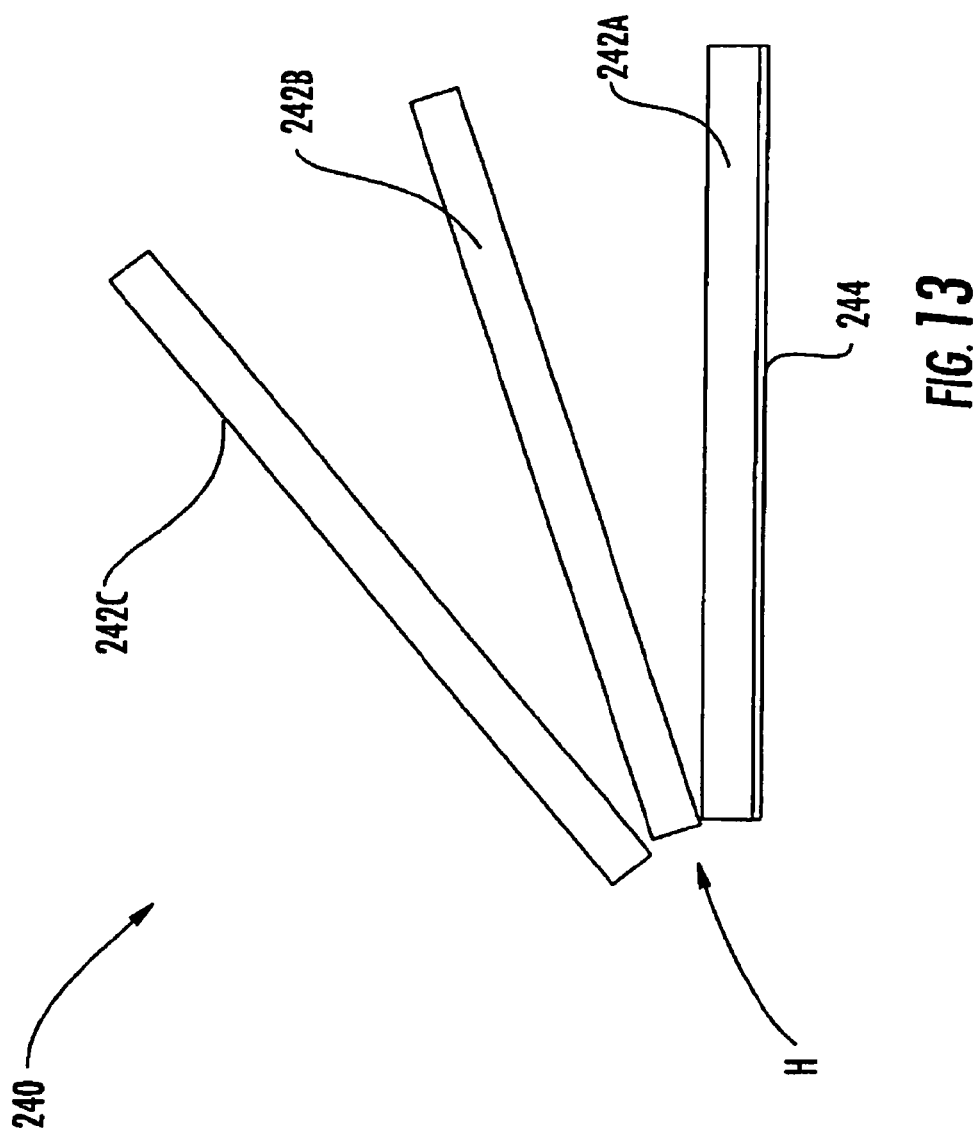

APPARATUSES AND SYSTEMS FOR DENSITY GAUGE CALIBRATION AND REFERENCE EMULATION

RELATED APPLICATIONS

This application is related to U.S. Provisional Patent Application Ser. No. 60/663,420, filed Mar. 18, 2005; and is a continuation of application Ser. No. 11/384,005 filed Mar. 17, 2006, now U.S. Pat. No. 7,705,614 the disclosures of which are incorporated herein by reference in its entirety.

TECHNICAL FIELD

The presently disclosed subject matter relates to standardization and calibration of electromagnetic devices. More particularly, the presently disclosed subject matter relates to apparatuses and systems for emulating electrical characteristics of a material having a known dielectric constant.

BACKGROUND

Pavement materials, such as soil, sand, aggregate, asphalt, and cement, typically require quality control testing during the construction process for physical attributes such as density, modulus, cement content, and moisture. The moisture and density relationship is an important property that is monitored during road construction and rehabilitation. In order to provide durable roads, the soil base layer and all hot mixed asphalt layers above it are compacted to density values that are specified in the engineering design. Destructive tests and nondestructive tests are used throughout the industry for quality control of these materials.

In laboratory tests, cylindrical samples are prepared, typically with a gyratory compactor, and various material properties are studied to determine the best mix design for a pavement. In field destructive tests, cylindrical samples are cored from test strips, newly constructed roads, or existing roads. The material properties of these samples are then used to evaluate whether the test strip or the new pavement meets the design criteria and whether the existing road is in good operating condition or in need of repairs.

Currently, several methods are used for measuring the density of cylindrical asphaltic samples including dimensional analysis, the water displacement method, and the paraffin-coated or para-film-covered method. In each case, the bulk density of a sample is derived by, as in the definition, dividing the dry sample mass by the estimated sample volume. All methods require a balance with a sensitivity of 0.1 gram to measure the mass of the sample.

In the dimensional analysis method, sample volume is determined from radius and thickness (height) measurements of the sample. Here, many readings of radius and thickness of the sample are made either manually using a vernier caliper or automatically using a laser system. The average values of radius and thickness are then used to calculate the sample volume. Other methods use the Archimedes Principle related to water displacement for determining the sample volume. These methods require a large container filled with clean water wherein the water temperature is monitored and controlled at a specific temperature, e.g. at 25 degrees Celsius. The sample is kept immersed in water for approximately 4 minutes during the test and the weight of the sample, while suspended in water, is recorded. In the "paraffin-coated" method, after determining the dry weight of the sample, a thin coating of paraffin is applied to cover the entire surface area of the sample. Then, the sample is weighed again in air. Finally, the sample is weighed while immersed in water. More details can be found in standards ASTM D 2726 for the water displacement method and ASTM D 1188 for the paraffin-coated method.

In the field, at present, the moisture content and density of materials are typically determined using two non-destructive test methods. One method uses radioactive materials or nuclear gauges and is commonly known as the "nuclear method". The other method uses the electrical response of the material without radioactive materials, using electromagnetic devices, and is commonly known as a "non-nuclear" method or the "electromagnetic method".

Nuclear radiation gauges, such as those described in U.S. Pat. Nos. 2,781,453 and 3,544,793 have been widely used for measuring the density of soil and asphaltic materials and have been in use in the road construction industry since the 1950's. Such gauges employ a nuclear radiation source, typically a mono-energetic source, which directs gamma radiation into the test material, and a radiation detector, typically a Geiger Mueller tube, located adjacent to the surface of the test material for detecting radiation scattered back to the surface. The gamma radiation interacts with matter in the test material, either by losing energy and changing direction (Compton interactions) or by terminating (photoelectric interactions). Consequently, the gamma radiation detected by the radiation detector has a continuous energy spectrum. From this detector reading, the density of the material can be determined.

These gauges are designed to operate both in a "backscatter" mode and in a direct transmission mode. The radiation source is vertically moveable from a backscatter position where it resides within the gauge housing (e.g., the nuclear gauge rests on the surface of the pavement or soil) to a series of direct transmission positions where it is inserted into small holes or bores in the test material (e.g., the nuclear source is inserted beneath the soil surface, as in a borehole). The gamma radiation received by the radiation detector is related to the density of the test medium by an expression of the following form:

$$CR = A\exp(-BD) - C$$

where:
CR=count ratio (the accumulated photon count normalized to a reference standard photon count for purposes of eliminating long term effects of source decay and electronic drift);
D=density of test specimen; and
A, B, and C are constants.

Nuclear gauges, however, require a high degree of training and radiological management for the operators of these gauges. Therefore, knowing of the desire to obtain accurate field measurement gauges without the use of nuclear gauges, research began in the late 1980s into electromagnetic devices for measuring the density and moisture content of road construction materials such as asphalt, soils and aggregates. These electromagnetic devices have different principles behind moisture and density measurements than their nuclear counterparts.

For moisture measurements in the field, the nuclear device method incorporates neutron moderation, which results in a measurement of the number density of the Hydrogen atoms present in the material. For non-nuclear devices, the moisture measurement is based on the electronic dipole moment per unit volume of the material under test. Most asphalt has a permittivity of less than about 8 and is not terribly dispersive with frequency. Typically, dry soil has an electrical permittivity of about 4, water about 80, and air about 1. In general, soil can have permittivities that range from a dry value of about 4 to a saturated value above 40. In soils, this parameter is frequency dependent. As the percent water increases in sand, soil, aggregate, etc., the dielectric constant increases as well. Therefore, the moisture content can be easily found by measuring the electrical properties of the material. A much more complicated process is required for simultaneous measurement of moisture and density values.

For density measurements in the field, the nuclear device method uses gamma ray scattering properties of the materials. At energies below 1 MeV, the amount of scattering in a material is directly proportional to the number density of electrons. Since the number density of electrons is related to the material density, by measuring the scattering, the material density is found. The electromagnetic device method uses permittivity changes resulting from the decrease in the air void content of an asphalt mix as it is compacted. Therefore, asphalt density can be estimated by measuring the permittivity of the mix.

Asphalt is a heterogeneous mixture of aggregate, binder, and air. Soil is much more complex and is a mixture of aggregate minerals, air, and water. Air has a dielectric constant $\in_r$ of 1.0, whereas dry aggregate and binder dielectric constant $\in_r$ is about 4.0. Water has a dielectric constant $\in_r$ of near 80 depending on the temperature and purity of the water. The dielectric constant or permittivity is represented by a complex number where the real part represents the energy stored and the imaginary part represents the energy loss in the material. For asphalt, as compaction increases and the density increases, the air voids decrease and the dielectric constant increases. As such, asphalt is mostly moisture free and usually has a simple frequency response. For soil, increasing compaction efforts also increases the dielectric constant. However, soil is a complex heterogeneous mixture of air, water, and solid minerals that has a very complex frequency response that complicates the response. As a result, for soil, measurements of the real and imaginary parts of the permittivity are required to separate the moisture from the density effects. Hence, the frequency response of these materials is also of major interest.

For a given soil, the maximum compaction is achieved at specific moisture content. In the laboratory, the density-moisture content relationship for a soil is determined using the industry standard "Modified Proctor Method", otherwise known as ASTM D 1557 or the "Standard Proctor Method" known as ASTM 698.

For asphalt, in the laboratory there are three methods of designing/analyzing asphalt mixes: (1) The Marshall method; (2) the Hveem method; and (3) the Superpave method. All three methods produce cylindrical asphalt cores for analysis. One of the most important factors is the material density, which is a primary property in the selection of the best mix design. The material density of cylindrical asphalt specimens is determined using dimensional analysis (mass over volume) or variations of water displacement methods as specified in ASTM standards D 1188 and D 2726.

A particular asphalt mix will contain unique aggregate types, textures, binder, and also contain air voids. For instance, the aggregate may be one of limestone or granite, and have proportions of size and texture from passing the 200 sieve to 25 mm. As a result, the base dielectric constant of a high air void mix may be 4 for one mix and 7 for another. Furthermore, the dielectric constant will only change a small percent as the air void content is decreased by compaction. For example, low to high density may range from 4.0 to 4.7 in the real part of the permittivity.

FIG. 1 illustrates different mixing series and how they encompass different "base" dielectric constants for each mix. In FIG. 1, each line represents the entire dielectric range from low to high density of that species or mix. Furthermore, although there are different intercepts for each mix, the slopes are not much different. The mixes shown in FIG. 1 include both granite and limestone aggregates.

As discussed above, the industry has recently become interested in electromagnetic devices for quality testing of pavement materials. Examples of such electromagnetic devices include Model M2701B manufactured by Troxler Electronic Laboratories, Inc., the assignee of the present subject matter, and Model PQI 301 manufactured by TransTech Systems, Inc. Both of these gauges use a single frequency (continuous) source which can be modulated, wherein the M2701B operates at about 50 MHz and the PQI 301 operates at a much lower range frequency. These devices are planar in that they are placed on top of the surface to be measured and fringe a field of energy into the material of interest. Typically, a high frequency electrical signal is passed through the capacitive-sensor placed on the testing material. The signal characteristics measured by electrical signal detection circuitry are then compared with those obtained by placing the sensor on known materials. A correlation to the material density is then used to estimate the density.

Other electromagnetic devices include the TDR as sold by Durham Geo Slope Indicator; ground penetrating radar or GPR; resistive devices such as that marketed by Humbolt and described in U.S. Patent Application Publication No. 2004/0095154; swept or stepped frequency devices such as that manufactured by Greer and described in U.S. Pat. No. 6,388,453; and microwave systems including systems described in U.S. Pat. Nos. 6,316,946 and 5,952,561 and U.S. Patent Application Publication No. 2005/0150278. Electromagnetic devices that operate in the "backscatter" as well as "transmission" mode are also envisioned with bandwidths of several GHz, such as the device described in U.S. Patent Application Publication No. 2005/0150278.

Moisture sensors can be stand-alone versions as well as dual density/moisture probes. Two examples of the stand-alone moisture probes are capacitance monitors for soil moisture as described in U.S. Pat. Nos. 5,260,666 and 4,929,885; each of which is assigned to the assignee of the present subject matter, Troxler Electronic Laboratories, Inc. Another class of electromagnetic moisture probes is manufactured by Hydronix.

Because of variations in manufacturing tolerances, sensing probes of the same design will not necessarily sense exactly the same values. Consequently, each sensing probe must be individually calibrated at the manufacturing factory and as a practical matter the probe should be periodically checked (or recalibrated) to assure that the calibration has been maintained.

For nuclear gauges, calibration is typically conducted using three large and heavy blocks of material of different densities. Typically, these blocks are aluminum (160 lbs/ft$^3$ or PCF), magnesium (110 lbs/ft$^3$), and a mix of aluminum and magnesium (135 lbs/ft$^3$). Other prior art in nuclear calibration devices include shielded capacitance standards as manufactured by Troxler Electronic Laboratories, Inc. and described in U.S. Pat. No. 4,924,173.

Electromagnetic gauges are typically factory calibrated using three large slabs or calibration standards (e.g., of a size 2 foot by 1 foot by 6 inches thick) of varying dielectric constants. Three reference data points are obtained and a least squares fit is applied to the data points for the straight-line equation. It is noted, for example, that the three calibration standards typically span the entire dielectric range shown in FIG. 1. In other words, an offset is usually necessary, but the slopes are going to be close to the expected field value.

Since the electromagnetic density gauges as known in the art are also operated on hot materials in the field, it is possible for the electrical properties of the sensor to change with use and time. Also, any changes in the components in the electrical circuitry of the gauge can lead to drifts in the detected electrical signals. Although the gauges have been designed to minimize these problems, the net effect can be significant to the user. As such, the electromagnetic gauges should periodically be recalibrated in the laboratory.

Electromagnetic gauges are typically recalibrated in the laboratory using bulk homogeneous materials of known electrical properties such as plastic, NYLON, PVC, PLEXIGLAS, and glass, to name a few. These materials are typically in the form of slabs with dimensions 12 inches by 12 inches by 6 inches wherein the weight of the standard can approach 130 pounds or more. Standards can also be calibrated using cylindrical specimens, much like the cores drilled in the field or made in the lab. In any case, the gauge is placed on each material and the signal characteristics are recorded. Using a mathematical model that relates the signal characteristics to the assigned density value, the calibration coefficients are then determined. The systematic errors determined can be corrected in the laboratory using the calibration standards. The measurements taken on the standards will show the changes and if the changes are small enough, adjustment to the calibration coefficients can be made. Hence, confirmation readings obtained on the standards will indicate if recalibration or a simple offset will be necessary. It is additionally known that many regulatory agencies now require that electromagnetic gauges have a reference standard for obtainment of these confirmation readings.

The response of electromagnetic gauges is related to the electrical properties of the material being tested. Therefore, calibration of the devices must typically be performed in the field at regular periodic intervals for determining the density and moisture content of materials. This calibration is typically correlated to known standards. For example, with density gauges, FIGS. 2A and 2B show the comparison of gauge readings of factory-calibrated gauges to true density values for various asphalt mixes (FIG. 2A relates to limestone mixes and FIG. 2B relates to granite mixes). Conversion of the direct reading to the absolute density reading can be performed using cores extracted from the pavement or nondestructively by comparing and correcting using a nuclear method.

For instance, the calibration equation for the M2701B device can be selected for different mix types as found empirically in the field. For example, the operator can do simple offsets or a full-blown slope-intercept calibration to arrive at the calibration equation. This is sometimes achieved using a "test" strip wherein cores are removed from the test strip with different compaction efforts. Other times, a good compaction effort is made and a core is removed and gauge read. The gauge is then offset with one core. Here, for example, the operator would obtain a reading using the M2701B device, remove a core sample, and test it for density properties in the laboratory. Another well-known method is to obtain simultaneous readings using both a nuclear gauge and the electromagnetic device. The nuclear results are used to obtain the calibration in the electromagnetic device. The calibration in the gauge for a simple mix is therefore a simple "y=mx+b" equation or even a "y=a+b*exp(-c*x)" relationship as is currently being explored. A single core or an average of multiple cores can be used for a simple offset. If a good spread of densities is obtainable, then both slope and intercept can be calculated using standard methods.

It is known that electromagnetic devices must also be referenced (calibration confirmed) in the field preferably daily to account for any daily variances encountered. In order to provide this capability in the field, for example, the Model M2701B comes with a "portable" standardization block as shown with reference to FIGS. 3 and 4. As shown in FIG. 3, this standard block S is typically made out three (3) slabs of glass G, each typically having dimensions of 6 inches wide by 6 inches long by 0.5 inches thick, wherein the slabs of glass G are glued together. Typically, a thin layer of FR4 glass epoxy laminate L is overlaid on top of the glass slabs to provide protection to the glass. The standard block S is typically installed with top and bottom layers of foam F in a carrying case C for the gauge device D (see FIG. 4 showing laminate L overlaid on standard block S).

There are several limitations of this prior art standardization block S including: (1) fragility—because of the nature of glass it is possible to damage the block during transport of the gauge, thus leading to erroneous readings; (2) manufacturability—several steps that involve gluing using extremely hot glue are required including one operation gluing the standard to shock absorbing thick foam material, another operation gluing foam to the bottom of the case, and another operation gluing a thin FR4 sheet on the top surface of the glass; (3) cost—the type of special glass used for the standard is expensive; (4) weight—the glass-stack standard alone is about 5 lbs.; (5) size—the standard is only slightly bigger than the gauge sensor head; (6) volume—the glass and foam occupy a large space in the case; (7) stability—due to the weight and cumbersome size of the standard, the glue can loosen over time thereby providing erroneous readings; and (8) accuracy—due to the finite thickness of glass (1.5 inches), the gauge reading shows a small dependence on the type material on which the standard is placed.

Thus, there remains a long-felt need for apparatuses and systems of density gauge emulation for the standardization of electromagnetic gauges in the field using easy to manufacture, low cost, durable materials with improved stability during transportation.

SUMMARY

The apparatuses and systems of the present subject matter relate to calibrating and confirming the calibration and operation of non-nuclear moisture-density quality control equipment, such as electromagnetic devices. The apparatuses can include a surface for supporting the gauge, and a material composite for simulating the dielectric properties of a construction material. The composite can consist of a matrix of conducting and non-conducting material sometimes referred to as an artificial dielectric. It is envisioned that surface gauges, as well as surface probing instruments, can be calibrated, re-calibrated or confirmed for operational standards.

Disadvantages of prior art calibration block systems include weight, bulkiness, and limited range of permittivity. With the apparatuses and systems of the present subject matter, lightweight, economical standards are available of considerable smaller volume. The emulator apparatuses and systems of the present subject matter have the ability to artificially decrease the size of typical reference standards, and artificially increase the effective dielectric constant of standards by adding materials near the sensor and embedded in the dielectric material. Positive attributes of the apparatus of the present subject matter include: (1) the ability to be used with devices that sit on the surface or just above the surface of the material being measured; (2) lightweight and field portable; (3) can easily be integrated into a carrying case for the gauge it is used with; (4) can exhibit a frequency response tailored to a response of a heterogeneous material like soil with particular dispersive properties; and (5) can be used with devices that are inserted into the soil or other material being tested.

It is envisioned that apparatuses and systems of the present subject matter can be used for the calibration of low frequency instruments, including static or quasi-static instruments, as well as high frequency instruments (into the microwave region). Due to the complexity of the frequency response of heterogeneous mixes of materials like soil and water, a wide band response measuring both the real and imaginary parts of the permittivity is sometimes necessary. This wideband response makes it possible to obtain multiple parameters such as density and moisture in soil.

In one embodiment of the present subject matter, an emulator apparatus for emulating electrical characteristics of a material having a known dielectric constant is provided. The emulator apparatus can comprise an electrically non-conductive layer having a dielectric constant less than the material dielectric constant and an electrically conductive layer adjacent the non-conductive layer.

In another embodiment of the present subject matter, a combination carrying case and emulator apparatus is disclosed. The combination can comprise a housing adapted for containing a dielectric sensitive probe wherein the housing has a base and a closeable cover. The combination can further comprise an emulator apparatus disposed within the housing for emulating electrical characteristics of a material having a known dielectric constant, wherein the emulator apparatus can include an electrically non-conductive layer having a dielectric constant less than the control material dielectric constant and an electrically conductive layer adjacent the non-conductive layer.

In yet another embodiment of the present subject matter, a system for calibration of a dielectric sensitive probe to account for changes in gauge geometry and other factors affecting gauge calibration accuracy is described. The system can comprise a plurality of emulator apparatuses for emulating electrical characteristics of a plurality of materials having different known dielectric constants. Each of the plurality of emulator apparatuses can comprise an electrically non-conductive layer having a dielectric constant less than the associated one material dielectric constant and an electrically conductive layer adjacent the non-conductive layer.

In a further embodiment of the present subject matter, an artificial dielectric for emulating the dielectric constant of a material is provided. The artificial dielectric can comprise a substrate matrix having a dielectric constant less than the material dielectric constant and an additive combined with the substrate, the additive having a dielectric constant higher than the material dielectric constant.

In a still further embodiment of the present subject matter, an artificial dielectric for emulating the frequency dependence of a material having a known dielectric constant is described. The artificial dielectric can comprise a liquid mixture comprising at least one part liquid having a dielectric constant less than the material dielectric constant and at least one part liquid having a dielectric constant higher than the material dielectric constant.

In another embodiment of the present subject matter, an adjustable emulator apparatus for emulating electrical characteristics of a material is provided. The emulator apparatus can comprise an electrically non-conductive layer having a dielectric constant and an adjustable electrically conductive layer adjacent the non-conductive layer and defining an air gap there between. The conductive layer is adjustable toward the non-conductive layer to increase the measured dielectric constant and is adjustable away from the non-conductive layer to decrease the measured dielectric constant.

In yet another embodiment of the present subject matter, an emulator apparatus for emulating electrical characteristics of a material having a known dielectric constant is provided. The emulator apparatus can comprise a first electrically non-conductive layer having a dielectric constant approximately equal to the material dielectric constant and at least one second electrically non-conductive layer having a dielectric constant greater than or equal to 1.0, the at least one second non-conductive layer adjacent the first non-conductive layer.

In a further embodiment of the present subject matter, a combination carrying case and emulator apparatus is described. The combination can comprise a housing adapted for containing a dielectric sensitive probe wherein the housing has a base and a cover. The combination can further comprise an emulator apparatus disposed within the housing for emulating electrical characteristics of a material having a known dielectric constant, wherein the emulator apparatus can comprise a first electrically non-conductive layer having a dielectric constant approximately equal to the material dielectric constant and at least one second electrically non-conductive layer having a dielectric constant greater than or equal to 1.0, the at least one second non-conductive layer adjacent the first non-conductive layer.

Therefore, it is an object of the present subject matter to provide apparatuses and systems for emulating electrical characteristics of a material having a known dielectric constant for the standardization and calibration of electromagnetic gauges.

Several objects of the presently disclosed subject matter having been stated hereinabove, and which are addressed in whole or in part by the presently disclosed subject matter, other objects will become evident as the description proceeds when taken in connection with the accompanying drawings as best described hereinbelow.

BRIEF DESCRIPTION OF THE DRAWINGS

FIG. 10 is a photograph illustrating a reference emulator installed in a carrying case of an electromagnetic gauge in accordance with an embodiment of the present subject matter;

FIG. 12 is a cross-sectional view of a reference emulator calibrator consisting of reference emulators of varying thickness of the same material in accordance with an embodiment of the present subject matter;

FIG. 13 is a cross-sectional view of a reference emulator calibrator consisting of hinged non-conductive plates in accordance with an embodiment of the present subject matter;

DETAILED DESCRIPTION

Background of Artificial Dielectrics

Artificial dielectrics are basically large-scale models of a dipolar molecule, constructed by arranging conductors in a 3-D pattern. A lightweight binder of filler material such as polystyrene supports the conductors. The result is a manmade material that simulates an ordinary dielectric material with a dipole moment. The combined effect of all the individual conductors of the lattice is to produce a net dipole polarization P per unit volume. Artificial dielectrics are discussed extensively in the art, such as by W. E. Kock in "Metallic Delay Lines," *Bell System Technical Journal*, vol. 27, pp. 58-82 (1948) and by Robert E. Collin in "Field Theory of Guided Waves," Second Edition, IEEE Press (1991).

As shown in FIG. 5 (Collin), there are many shapes of conductors that one can use for artificial dielectrics, such as disks, needles, spheres, cylinders, etc. incorporated into a matrix. FIG. 5A illustrates a three-dimensional sphere medium; FIG. 5B illustrates a three-dimensional disk medium; FIG. 5C illustrates a three-dimensional strip medium; and FIG. 5D illustrates a three-dimensional rod medium. While FIGS. 5A-5D are shown as three-dimensional systems, it is understood that they could be configured as two-dimensional systems.

In the case of metal strips loaded periodically in a substrate (such as in FIG. 5C), the dielectric constant is anisotropic since the orientation of the electric field vector E can result in capacitive loading if perpendicular to the faces of the strips, or inductive loading if the fields are parallel to the faces. For the perpendicular case, the dielectric constant is increased resulting in what is also known as phase delay media. For the case where the strips behave inductively, (electric fields parallel to the faces), the magnetic moment leads to a reduction in the permeability. This is sometimes referred to as a phase-advance dielectric.

Figure 5A:
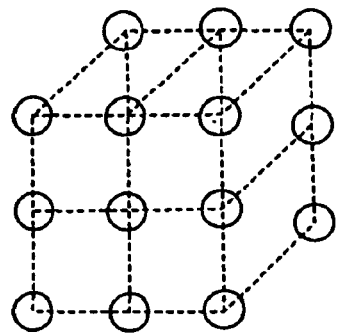
FIGS. 5A-5D are perspective views of prior art artificial dielectric structures (Collin)
Figure 5B:
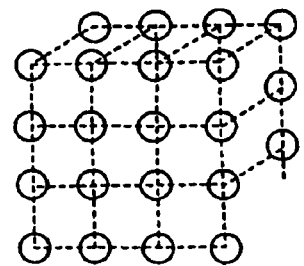
Figure 5C:
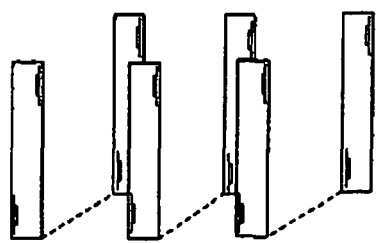
Figure 5D:
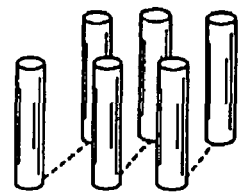

For electromagnetic devices such as the TROXLER M2701B (operated in VHF range) or TRANSTECH PQI 301 (operated in low frequency range), an artificial dielectric such as in FIG. 5C can be made simpler by joining the metal strips together in a sheet or plate. Alternatively, separate metal strips can be mounted with a board or other substrate on the bottom. While electromagnetic devices such as the M2701B or PQI 301 can be based on different operating principles (the M2701B measures coupling from one strip to another while the PQI 301 measures the capacitance), they each can be calibrated or referenced with these types of plates.

Figure 6A:
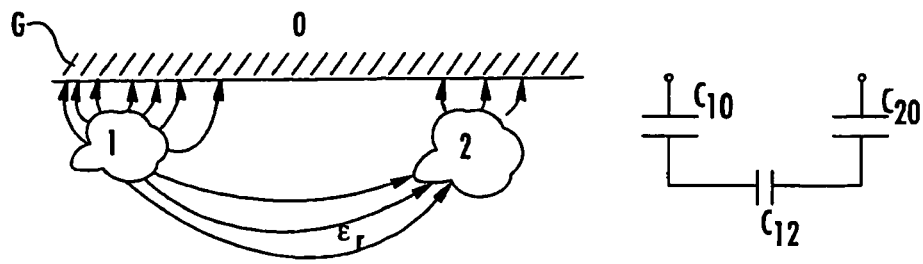
FIGS. 6A-6B are schematic and electrical diagrams of a capacitive device measuring a medium with and without a conductor, respectively, in the field proximity.
Figure 6B:
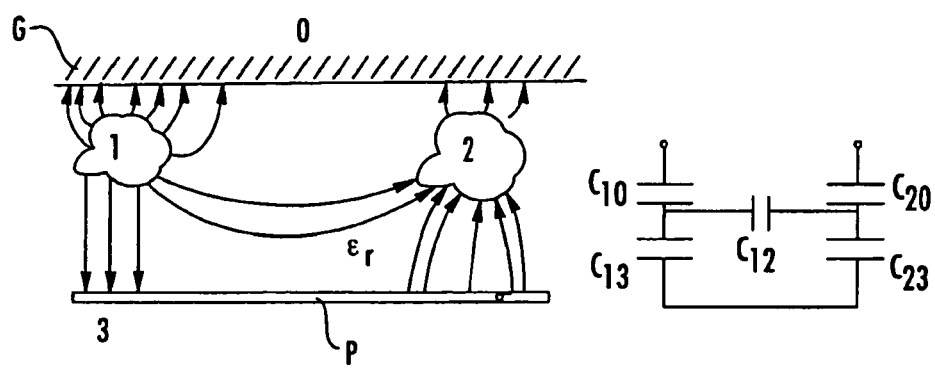

FIGS. 6A and 6B show general diagrams of a capacitive device like the PQI 301 measuring a medium with and without a conductor in the field proximity. FIG. 6A depicts a sensor on infinite medium $\in_r$ between nodes 1 and 2 with no conductor and where $C_{12}$ is the external capacitance known as the mutual partial capacitance. This is the result of the sensor field energy fringing into the asphalt or soil. $C_{10}$ and $C_{20}$ are parasitic capacitances that should be minimized for a good sensor design. $C_{10}$ is the capacitance to ground of one conductor, while $C_{20}$ is the capacitance to ground of another conductor. The signal ground G, represented by the node 0, could be a system ground, or isolated using electronic techniques, or it may act as a shield. $C_{12}$ represents the field energy of the desired measurement. Shields are sometimes incorporated so that changes in the dielectric constant $\in$ external to the sensor result in measurements of $C_{12}$ as opposed to changes in $C_{10}$ or $C_{20}$.

FIG. 6B depicts a floating conductor brought into proximity of two conductors, such as ground G (node 0) and plate P (node 3). In FIG. 6B, the conducting plate P is added at the bottom and the calibration device is bounded by conductor nodes 1 and 2 and conducting plate P (node 3). The network model shown in FIG. 6B results in $C_{12}$ being in parallel with the series capacitance $C_{13}$ and $C_{23}$. Hence, the coupling increases as the effective stored energy in the dielectric medium increases as modeled. In FIG. 6B, the effective capacitance is:

$$C_{eff} = C_{12} + (C_{13} * C_{23})/(C_{13} + C_{23})$$

$C_{eff}$ is generally greater than $C_{12}$ and therefore the effective capacitance and thus dielectric constant has increased. As such, if insulated from ground in this manner, the additional conductor acts to increase the measured capacitance coupling between nodes 1 and 2. It is noted that the permittivity of the medium does not change, it is artificially increased by the proximity of the conducting plate P. $C_{eff}$ is a function of $\in_r$ and t where $\in_r$ and t are bounded by nodes 3 and nodes 1 and 2.

In addition to the creation of an artificial dielectric by a sheet or a plate, another important method to obtain synthetic dielectrics is through the use of mixtures. One example would be to load a stycast epoxy with a high dielectric powder such as BaTi or TiO2. Manufacturers such as Cuming Corporation and Master Bond supply artificial dielectrics and ceramic filled epoxies such as these. Other companies sell a two-part epoxy loaded with a dielectric powder. These epoxies can be used to manufacture cylindrical standards to synthesize asphalt cores taken from the road or made in a gyratory compactor.

Figure 7:
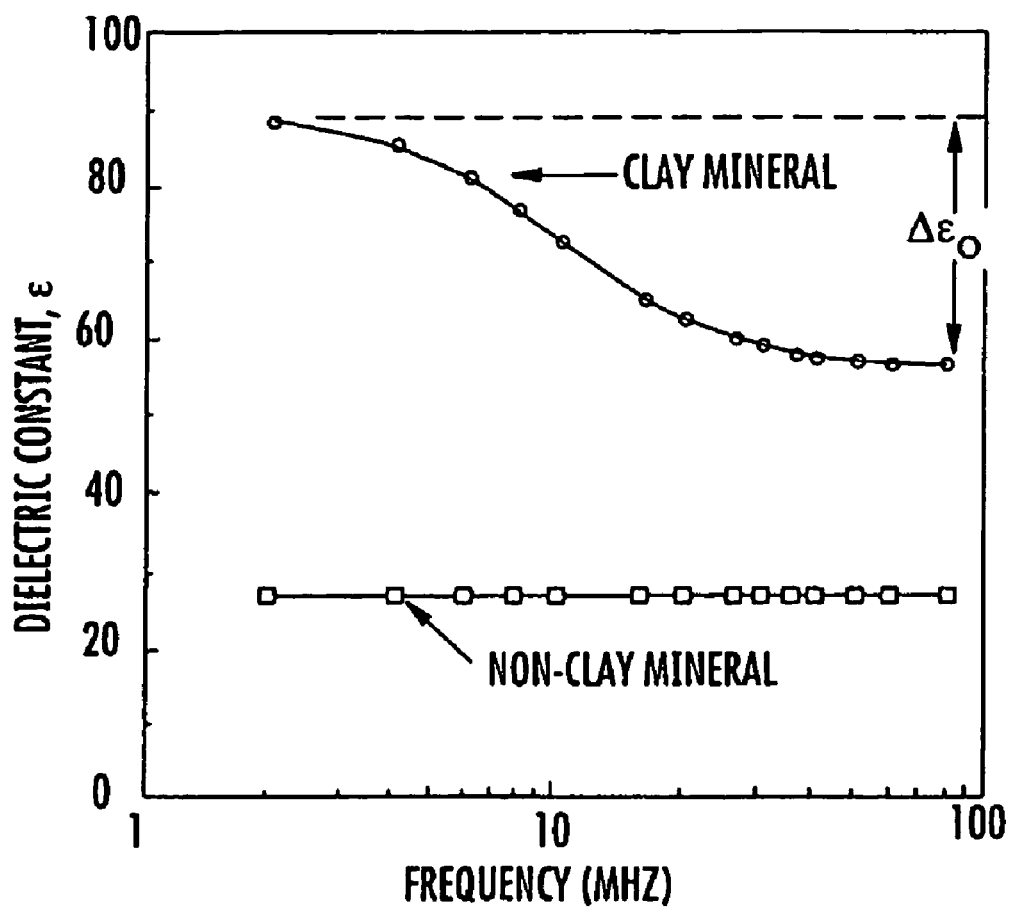
FIG. 7 is a graph illustrating dielectric constant $\in$ in relation to frequency (MHz) for different types of soils such as those measured by gauges used in conjunction with the reference emulator of the present subject matter (Arulanandan)

Liquids can also be used to model natural heterogeneous dielectric materials such as the soil profiles shown in FIG. 7 (Arulanandan). Soil/water mixtures have a complex frequency response that depends on the relative cohesiveness of the soil type and FIG. 7 illustrates measurements of the permittivity of different types of soils (e.g., cohesive soils such as clay mineral and non-cohesive soils such as sand). Soil can be modeled using an emulsion of water and oil. Many other types of mixtures such as gelatin, alcohol, etc. are also envisioned. Through mixture theory, these artificial materials will have adjustable dielectric properties for the real and complex parts of permittivity, including the frequency dependent parameter referred to as dispersion. For radiating devices, it is sometimes desirable to scale the model. For example, an antenna of higher frequency can mimic the lower frequency device if the proper scaling of the materials and dimensions surrounding the antenna is adapted. In practice, one may place a calibration probe into an analyzer (for solid/asphalt density or moisture), and insert the antenna into a small calibration tank. Impedance is obtained in this tank at a higher frequency, and then a mapping to the lower frequency device is performed. The tank in this case may also be surrounded with an absorbing material to simulate an infinite medium or half-space.

One of the many mixing formulas that has been successful in the art is by Briggeman as reported in "Dielectric Behavior of Heterogeneous Systems", Chapter 3, *Progress in Dielectrics*, Vol. 7 (1967). For oil in water emulsions at frequencies less than about 3 GHz, it has been shown that 3 parameters $\in$, $\sigma$, and F are used in the equations and represent the low frequency permittivity, conductance and frequency dependence, respectively. The conductivity of the solution is adjusted by changing the concentration of an electrolyte, such as sodium chloride. Mineral oil and water along with an emulsifier are used to adjust the dielectric constant. Briggeman's mixing formulas also have been shown to apply to the complex relative permittivity whereby $$\xi_r = \xi_r' + j\xi_r'' = \in_r - j\sigma/\omega\in_o$$

where sigma is the conductance, omega is the frequency in radians per second, and $\in_o$ is the permittivity of air. Briggeman's formula for lossy dielectrics becomes $$(\xi_r - \xi_{r1})^3/(\xi_{r2} - \xi_{r1})=(1-\Phi)^3 * \xi_r/\xi_{r2}$$

where $\xi_{r1}$ and $\xi_{r2}$ represent the disperse particle phase and the matrix phase, respectively, and $\Phi$ is the volume fraction of the disperse phase. By solving this equation for specific dielectric constants and conductance, soils such as clay can be synthesized including the frequency response. With proper mixing and materials, calibration standards for soils can be synthesized.

Emulator Apparatus

Figure 1:
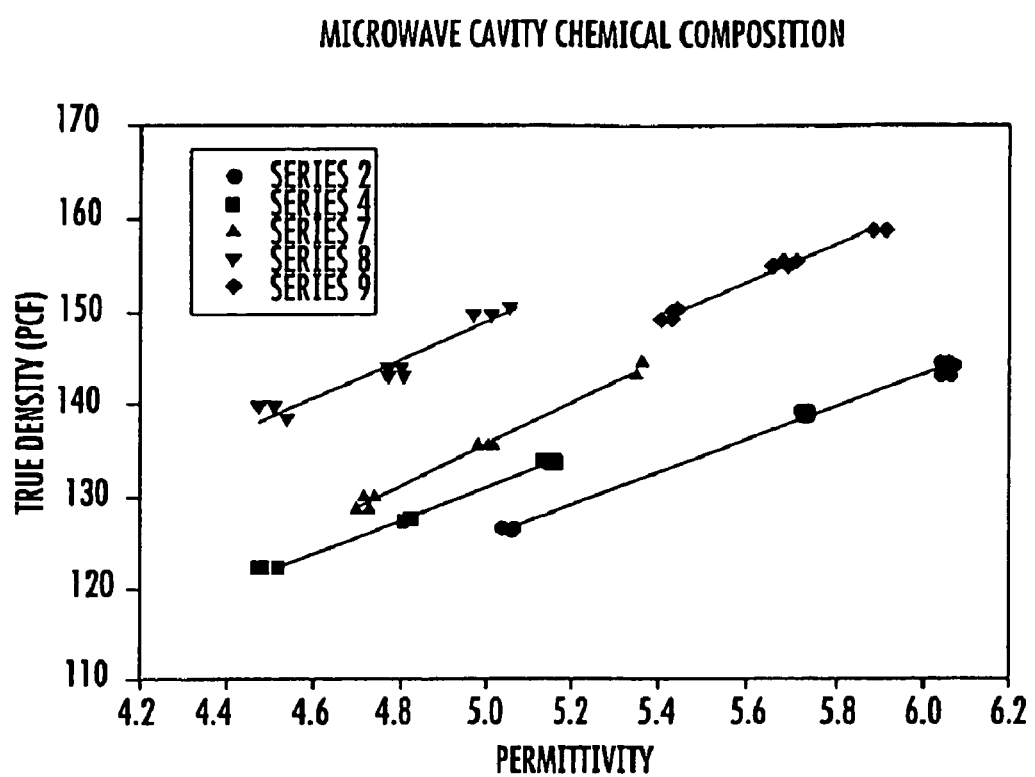
FIG. 1 is a graph illustrating true density in relation to permittivity for different mixing series of aggregates such as those measured by gauges used in conjunction with the reference emulator of the present subject matter.
Figure 2A:
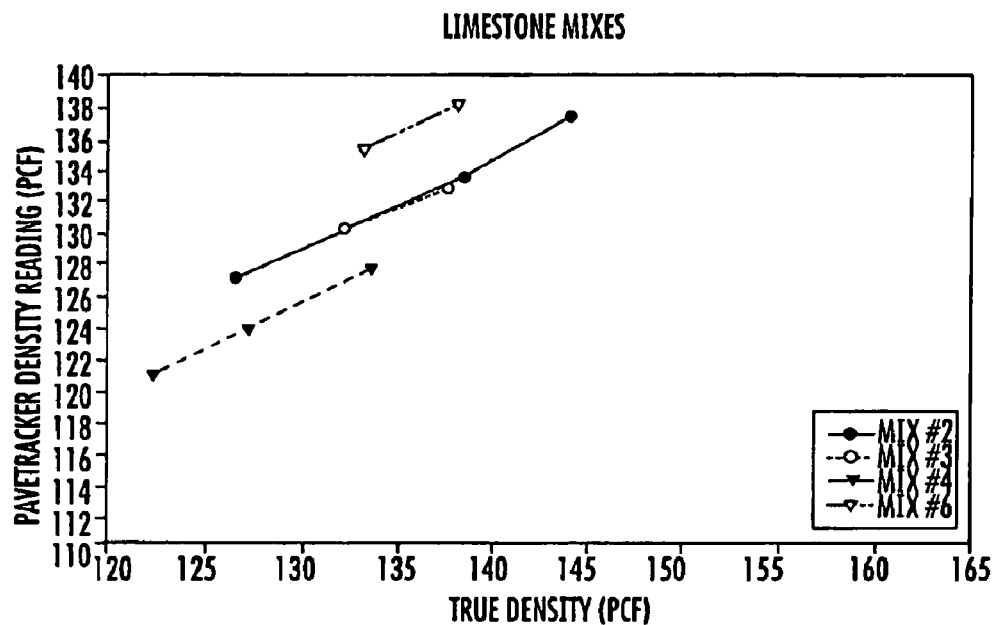
FIGS. 2A and 2B illustrate a comparison of gauge readings of factory-calibrated gauges to true density values for various asphalt mixes such as those measured by gauges used in conjunction with the reference emulator of the present subject matter.
Figure 2B:
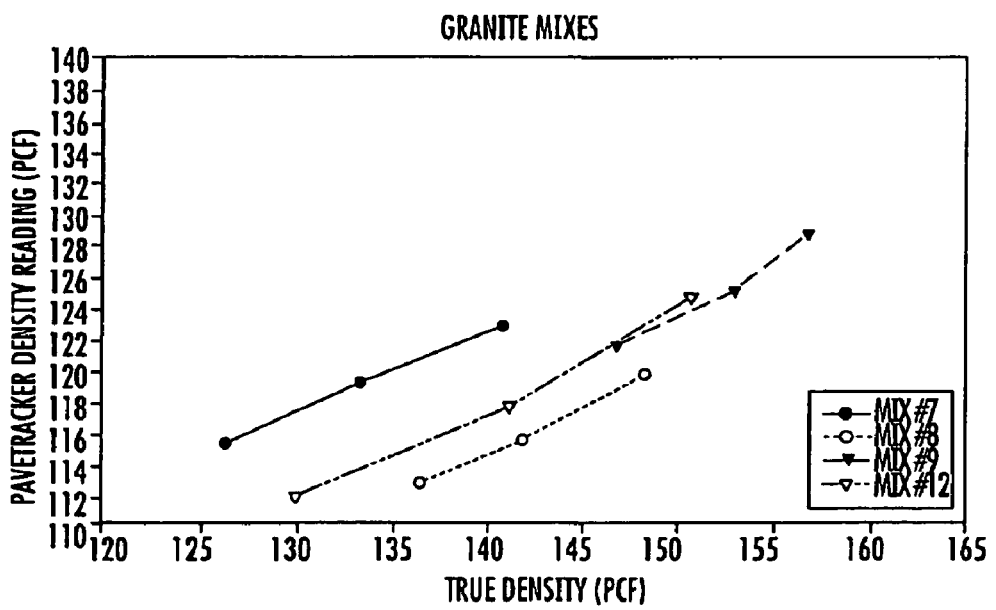
Figure 3:
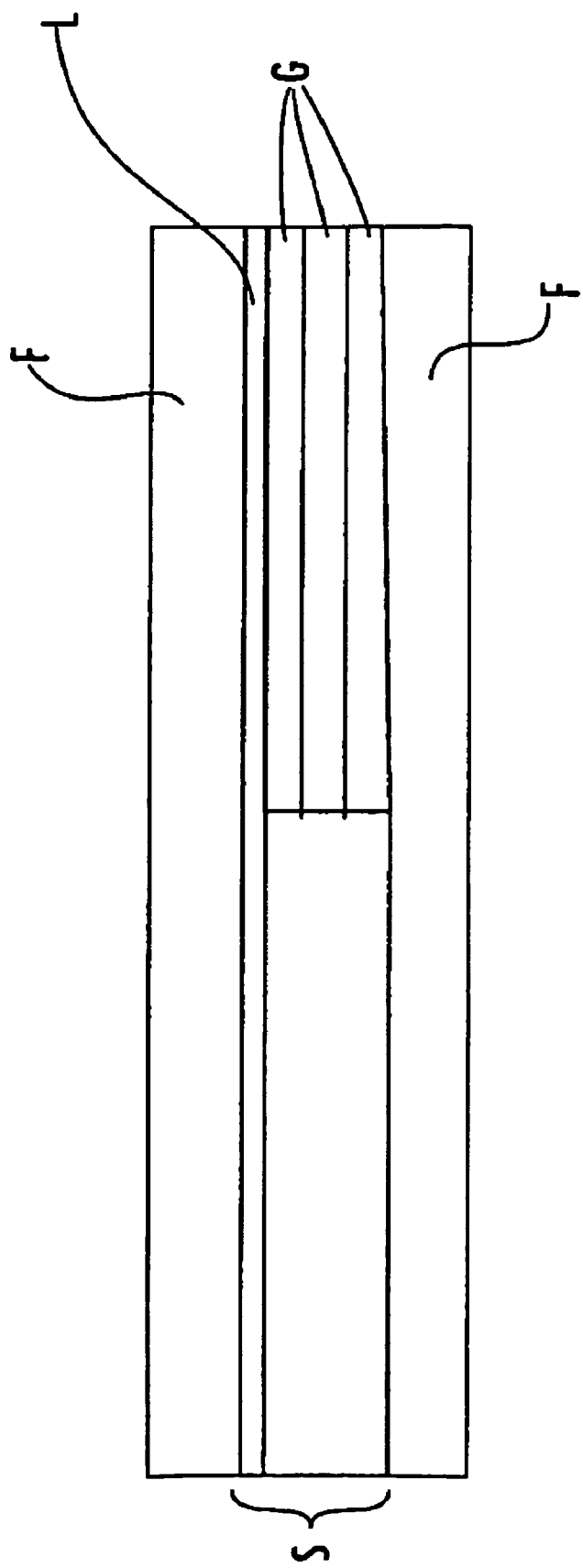
FIG. 3 is a side profile view illustrating a prior art standardization block.
Figure 4:
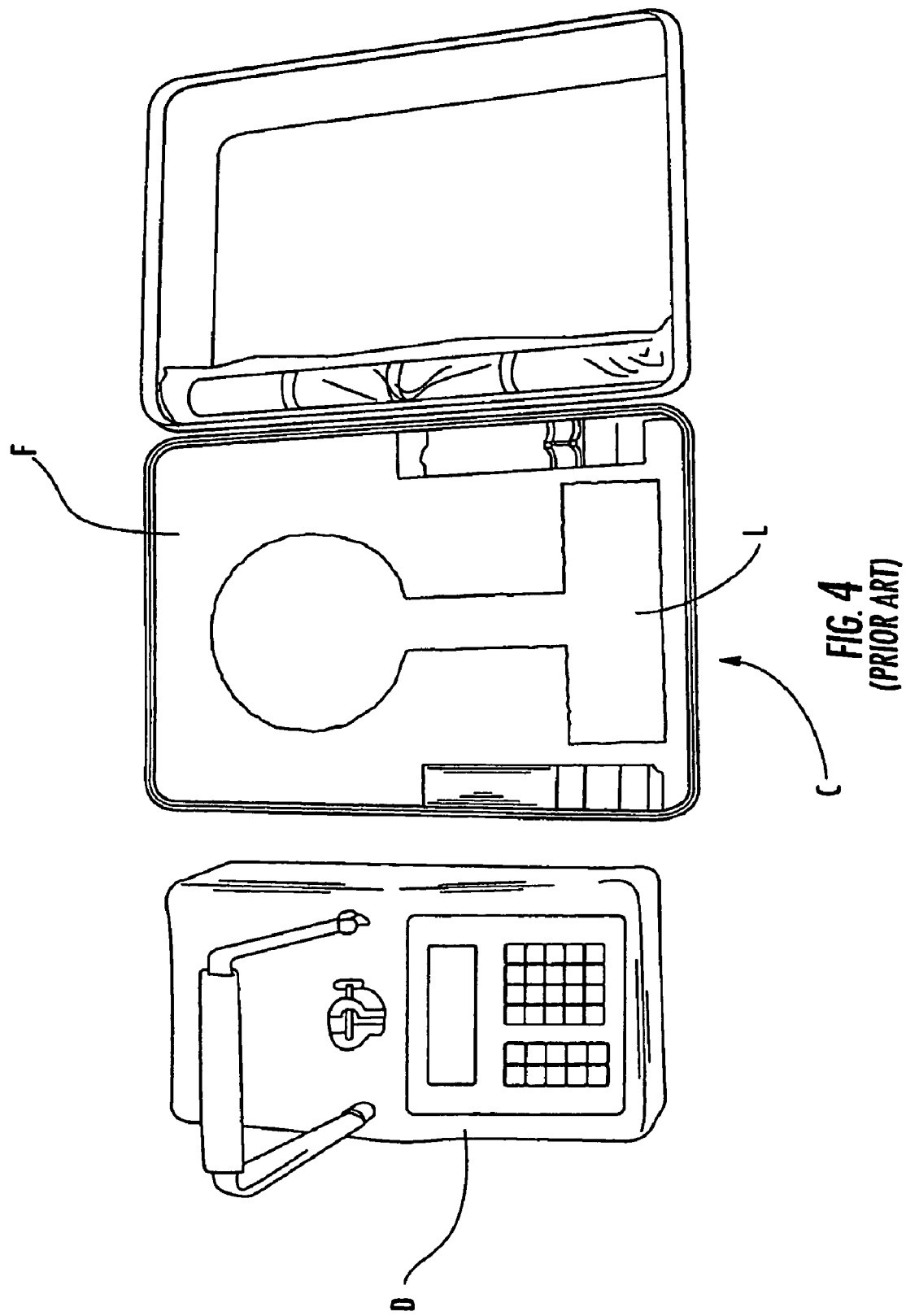
FIG. 4 is a photograph illustrating a prior art standardization block installed in a carrying case of an electromagnetic gauge.

In accordance with the present subject matter, an emulator apparatus is envisioned for providing a low-cost, lightweight, easily adaptable substitute for standardization blocks used in the prior art (see FIGS. 3 and 4). It has been observed that when an electromagnetic gauge is placed on a non-conducting material of dielectric constant $\in$ in the form of a slab with thickness t, the signal amplitude detected by the gauge is larger when the bottom surface of the material is covered with a conducting material. Thus, by selecting $\in$ and t, this composite slab can be used to emulate the dielectric property of material of much higher dielectric constant than the sum of the parts. This includes materials that can be used for gauge standardization (calibration confirmation) as well as calibration or recalibration of the gauge (in the field or otherwise).

Figure 8:
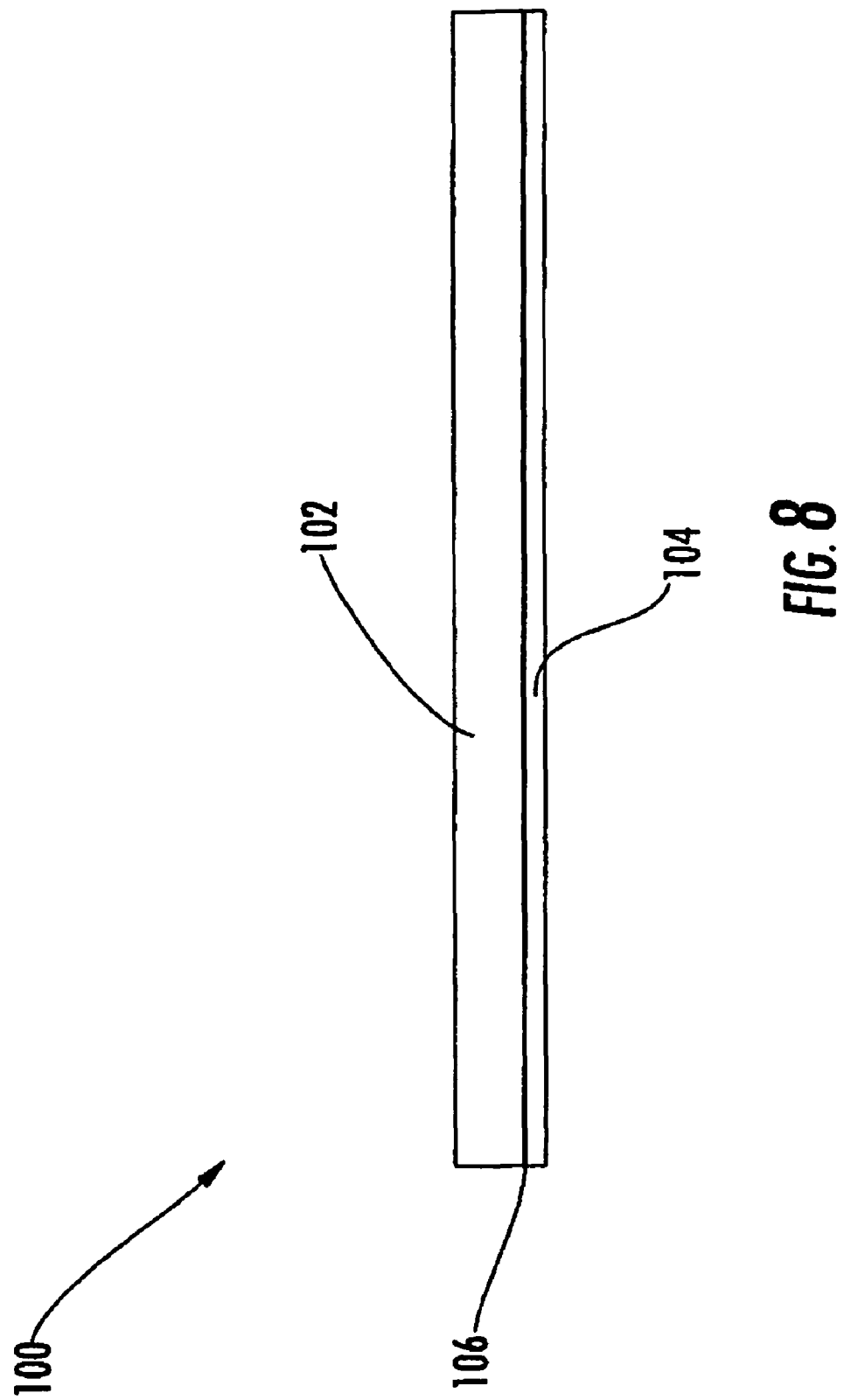
FIG. 8 is a cross-sectional view of a reference emulator in accordance with an embodiment of the present subject matter.

With reference to FIG. 8, a reference emulator, generally designated 100, is shown in accordance with one embodiment of the present subject matter. Emulator 100 is capable of emulating the electrical characteristics of a material having a known dielectric constant and typically comprises an electrically non-conductive layer (dielectric) 102 having a dielectric constant less than the known material dielectric constant and an electrically conductive layer 104 adjacent non-conductive layer 102. Electrically non-conductive layer 102 can be a plate constructed of any non-conductive material, such as, for example, fiberglass, plastics, ceramics, polymers, glass, and composites thereof. Electrically conductive layer 104 can also be a plate constructed of any conductive material, such as, for example, aluminum, copper, nickel, tin, silver, and steel. Non-conductive layer 102 and conductive layer 104 can be joined together by any method of joining two substrates, such as, for example, gluing. Furthermore, a thin, absorbent lossy layer 106 can be optionally positioned between non-conductive layer 102 and conductive layer 104. Lossy layer 106 can operate to reduce effects of air gaps, etc. sometimes experienced once non-conductive layer 102 and conductive layer 104 are joined together.

Referring further to emulator 100 illustrated in FIG. 8, several example emulator embodiments were designed using varying materials and thicknesses of non-conductive layer 102 and conductive layer 104 as follows.

In a first example, a Model M2701B gauge manufactured by Troxler Electronic Laboratories, Inc. was used to assign densities to four (4) emulators made with PVC as dielectric non-conductive layer 102 (varying in thickness) and a sheet of 0.025 inch thick aluminum as conductive layer 104. As shown in the table below, the measured densities at different thicknesses of non-conductive layer 102 covers the entire operational density range of the gauge.

| Emulator No. | Thickness of the dielectric material in non-conductive layer (inch) | Emulated Density (lbs/ft³) |
| --- | --- | --- |
| 1 | 1.000 | 109.2 |
| 2 | 0.750 | 117.8 |
| 3 | 0.500 | 139.0 |
| 4 | 0.375 | 161.1 |

In a second example, a Model M2701B gauge manufactured by Troxler Electronic Laboratories, Inc. was used to assign densities to two (2) emulators made with 0.75 inch thick DELRIN or FR4 as dielectric non-conductive layer 102 (i.e., same thickness but different material) and a sheet of 0.025 inch thick aluminum as conductive layer 104. The measured densities were as follows.

| Dielectric material | Emulated Density (lbs/ft³) |
| --- | --- |
| DELRIN | 126.0 |
| FR4 | 142.0 |

In a third example, a Model M2701B gauge manufactured by Troxler Electronic Laboratories, Inc. was used to assign a density to an emulator comprising a one-side copper cladded 8 inch×8 inch×0.75 inch FR4 slab. In this embodiment, the FR4 material worked as dielectric non-conductive layer 102 and the very thin copper plating worked as conductive layer 104. The measured density for this composite was 150 lbs/ft³.

Figure 9:
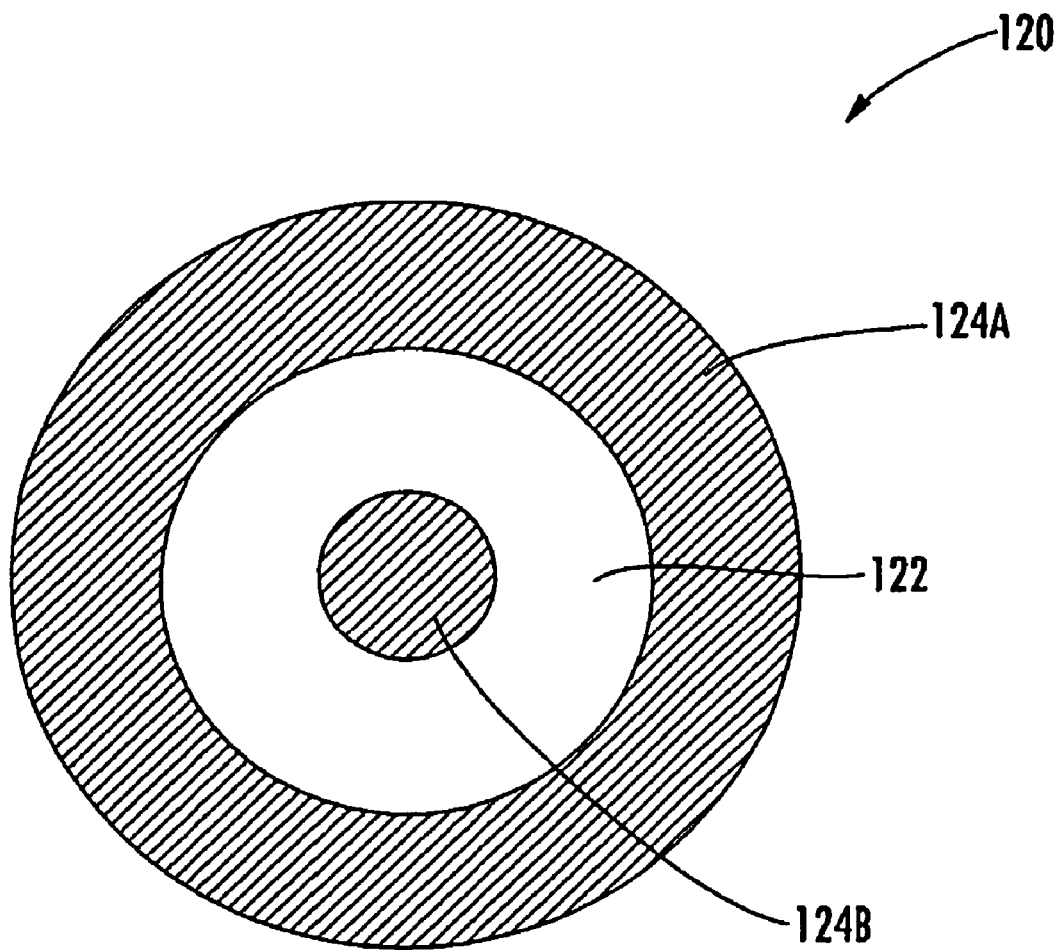
FIG. 9 is a top view of a reference emulator in accordance with an embodiment of the present subject matter.

While FIG. 8 illustrates non-conductive layer 102 and adjacent conductive layer 104 in a composite plate configuration to form emulator 100, it is also envisioned that the reference emulator of the present subject matter could be of a cylindrical configuration as shown in FIG. 9. In FIG. 9, emulator 120 is also capable of emulating the electrical characteristics of a material having a known dielectric constant and can comprise an electrically non-conductive layer 122 having a dielectric constant less than the known material dielectric constant and electrically conductive layers 124A, 124B adjacent non-conductive layer 122. In this embodiment, conductive layers 124A, 124B consist of an outer shell (124A) and a center radius (124B) and surround non-conductive layer 122.

It is understood that a plate on the bottom (not shown) could also be a conductor, and the shown metallic sections 124A, 124B could be insulators as well. For example, center radius 124B could be a dielectric material and outer shell 124A could be a conductor. Alternatively, outer shell 124A and center radius 124B could be of a higher dielectric constant than middle layer 122, thus forming a matrix.

Referring to FIG. 10, it is contemplated that an emulator of the present subject matter, such as emulator 100 shown in FIG. 8, can be combined with a carrying case C (such as shown in FIG. 4) that is used to house a dielectric sensitive probe, such as electromagnetic device D. The carrying case can comprise a base B and a closeable cover CC and can be constructed of any material as known in the art, such as metal or moldable plastic. Foam material F can further be included in the combination in order to provide protection to device D. This combination would allow the improved reference emulator to be carried into the field with the electromagnetic device for field referencing without the necessary weight and bulkiness seen in existing reference standard/carrying case combinations.

As discussed above, the emulator apparatus of the present subject matter has many advantages over the prior art. Since the thickness necessary is smaller than for bulk materials, the reference plate area can be increased without substantially increasing the weight of the entire unit. For example, for standardization (calibration confirmation) of an electromagnetic gauge, an 8" by 8" reference slab (instead of the 6" by 6" slab of the prior art design) can be used without a substantial increase in weight. This ability to increase the reference plate area minimizes errors from spatial variability of the signal characteristics of the gauge, a disadvantage found in using existing reference standards (the conductive layer also eliminates the influence of the bottom earth layer on the measurement). Other advantages include: lower cost for materials due to the wide range of commercially available polymer materials that are suitable for the purpose of reference emulation in accordance with the present subject matter; less fragile than current reference standard designs (which typically are made of glass); and ease in manufacturing due to less components needing to be assembled than in current designs.

It is envisioned that the emulator apparatus of the present subject matter can be used with varying types of electromagnetic devices. For example, some devices use a radial or coaxial configuration with a dielectric layer sandwiched between radii $r_1$ and $r_2$. As the dielectric thickness reduces, the effective dielectric constant will increase. Other instruments utilize resistive techniques. Still other methods, such as the time domain reflectometry (TDR) method, are based on wave propagation velocity and signal attenuation. In the TDR method, a wave propagates along a transmission line. The higher the dielectric constant, the slower the wave and the longer it takes for the signal to return. By knowing the length of the transmission line, and measuring the time for a step or impulse response to return, the dielectric constant can be calculated. The imaginary part of the dielectric constant is also found by looking at the loss of the wave, and the final and initial voltages. Liquid emulators may be ideal for TDR probe calibration. The TDR probes could also be permanently mounted in a cylinder of an artificial dielectric mixed with epoxy. Here the TDR rods would be in contact with the epoxy mix and calibration of the TDR head electronics and cabling could be achieved.

Calibration Confirmation and Recalibration

As described above, because of variations in manufacturing tolerances, sensing probes, such as electromagnetic devices, of the same design will not necessarily sense the same reading or same effective dielectric constant. Consequently, each sensing probe must be individually calibrated at the manufacturing factory. Since the response of electromagnetic gauges is related to electrical properties of the material being tested, it is known that electromagnetic devices must also be referenced (calibration confirmed) in the field preferably daily to account for any daily variances encountered. Furthermore, calibration of the devices must typically be performed in the field at regular periodic intervals for determining the absolute density and moisture content of materials. It is envisioned that the composite reference emulators of the present subject matter can be used for gauge calibration verification and calibration at the operators end (e.g., in the field).

A single emulator apparatus of the present subject matter (such as that described above with reference to FIG. 8) can be used to perform calibration confirmation. For example, if an operator measures the reference emulator standard just after calibration of the gauge in the factory and the standard reading is 150 lbs/ft$^3$, this value becomes the baseline for all future calibration confirmation readings. If at a later time, for example several weeks later, the operator again checks the reference emulator standard and the reading is 150.3 lbs/ft$^3$, the operator knows that the readings must be corrected in order to gather the correct density of the material being tested. Based on these measurements, any future readings R by the gauge on the test material must be corrected to R−(150.3−150.0) lbs/ft$^3$.

With reference to FIGS. 11A-11C, 12, and 13, a plurality of reference emulators can be used as a system for field calibration (or recalibration) of a gauge should a calibration confirmation as described above determine that calibration is needed. This recalibration may be deemed necessary, for example, if a calibration confirmation reading of 152.4 lbs/ft$^3$ is obtained, which would indicate that the gauge is "off" by over 2 lbs/ft$^3$ in relation to the 150 lbs/ft$^3$ original baseline standard. It is understood that any standard criteria, such as 1 lb/ft$^3$, 2 lbs/ft$^3$, etc. from a corresponding initial standard baseline reading (e.g., 150 lbs/ft$^3$) may be established for determining when recalibration is necessary.

Figure 11A:
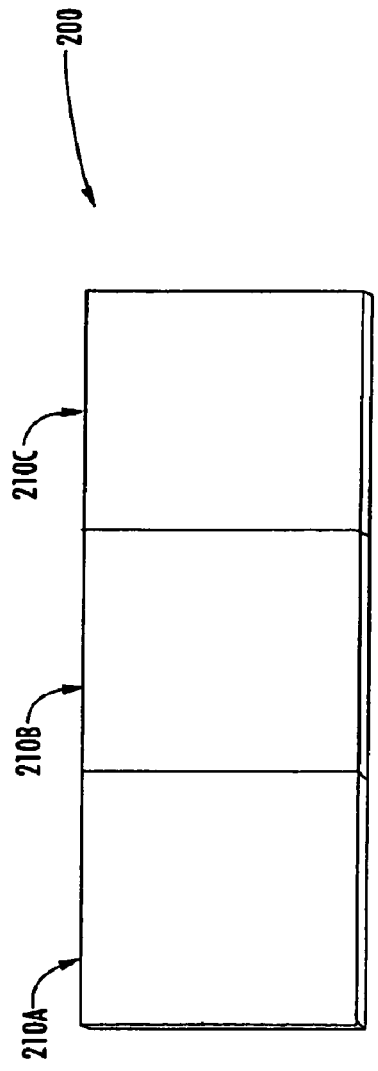
FIGS. 11A-11C are top plan and cross-sectional views of a reference emulator calibrator consisting of reference emulators of varying materials with the same thickness in accordance with an embodiment of the present subject matter.
Figure 11B:
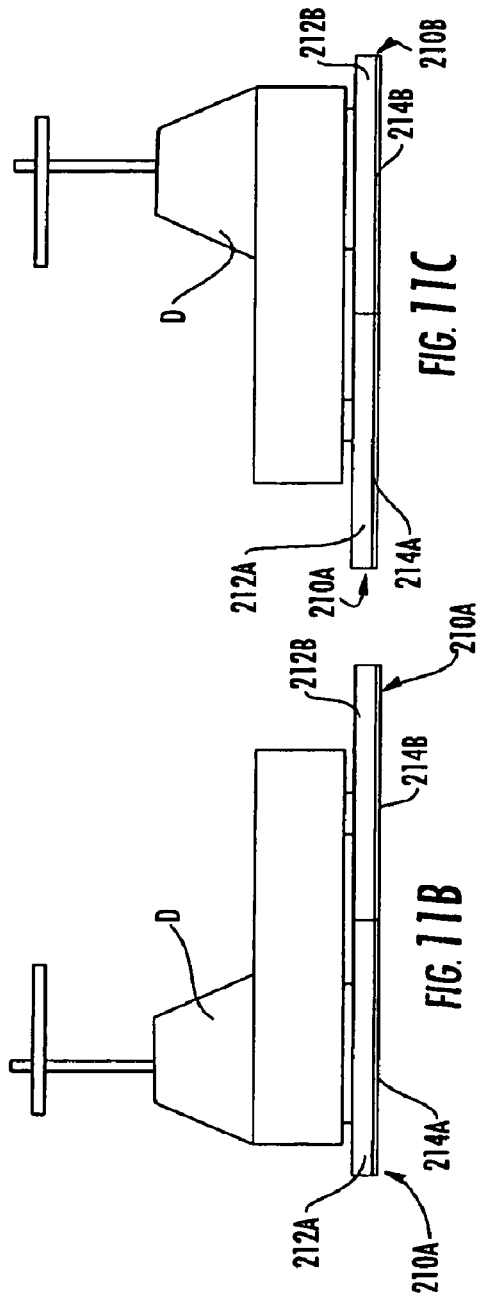
Figure 11C:
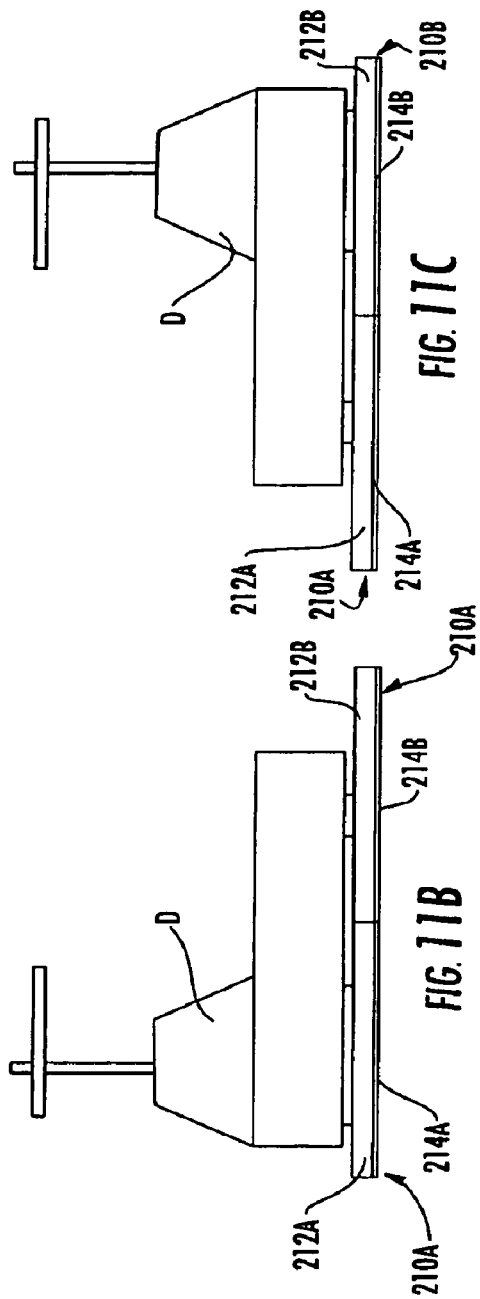

With reference to FIGS. 11A-11C, one embodiment of a calibration system is shown. Using this system, when a gauge is received from the manufacturer (i.e., after factory calibration), the operator can take measurements on an emulator calibrator 200 that consists of, for example, a set of three reference emulators generally shown as first emulator 210A, second emulator 210B, and third emulator 210C. Emulators 210A, 2106, 210C can be separate or integrated together in one unit. Similar to the apparatus described above with reference to FIG. 8, emulators 210A, 210B, 210C can each comprise an electrically non-conductive layer (layers 212A, 212B shown in FIGS. 11B and 11C) and an electrically conductive layer (layers 214A, 214B shown in FIGS. 11B and 11C) adjacent the non-conductive layer. As shown in FIG. 11A-11C, emulators 210A, 210B, 210C of emulator calibrator 200 can be of the same thickness but varying in materials of different dielectric constants (thus varying the density values). Alternatively, and as shown in FIG. 12, emulators 210A, 2106, 210C of emulator calibrator 200 can be of the same material (similar dielectric constant) but varying in thickness (thus varying the density values).

Referring back to FIGS. 11A-11C, once measurements are taken on emulators 210A, 210B, 210C, density values D1, D2, D3, respectively, are assigned. Periodically, for example on a daily or weekly basis, the operator can measure the density values of one or more of emulators 210A, 210B, 210C and compare these measured values with the initially assigned density values D1, D2, D3. Based on a standard criteria, for example when the current measurements show a deviation of more than 1 lbs/ft$^3$ from the corresponding initial values D1, D2, D3, the operator can perform a field calibration using calibrator 200. While calibration using a "three block system" is known in the art and described above, the field calibration using calibrator 200 discussed herein involves placing the gauge device D on each of emulators 210A, 210B, 210C to obtain new reference measurement readings (FIG. 11B illustrates device D taking a reading on first emulator 210A and FIG. 11C illustrates device D taking a reading on second emulator 210B). These new readings are then used in a least squares fit analysis to arrive at new calibration coefficients for the gauge. A calibrator system utilizing emulators of the present subject matter thereby gives the operator the ability to recalibrate the gauge efficiently in the field without the need to ship the gauge back to the factory for calibration.

With reference to FIG. 13, a further embodiment of a reference emulator calibrator in accordance with the present subject matter is illustrated generally as 240. In this embodiment, emulator calibrator 240 comprises electrically non-conductive layers 242A, 242B, 242C (of the same or varying thicknesses and of any non-conductive material as discussed above) joined by a hinged section H. The first non-conductive layer 242A can have an electrically conductive layer 244 (of any conductive material as discussed above) adjacent to it for the emulation of a first density D1. Second non-conductive layer 242B can be placed on first non-conductive layer 242A in order to emulate a second density D2 (by increasing the thickness). Furthermore, third non-conductive layer 242C can be placed on second non-conductive layer 242B and first non-conductive layer 242A in order to emulate a third density D3 (by increasing the thickness). In this arrangement, any number of densities can be emulated with the use of one conductive layer 244 and a plurality of non-conductive layers 242A, 242B, 242C. It is understood that while FIG. 13 illustrates the use of three non-conductive layers 242A, 242B, 242C, for the emulation of three different densities D1, D2, D3, any number of non-conductive layers could be arranged in a similar manner to emulate varying densities (i.e., two non-conductive layers to emulate two densities, four non-conductive layers to emulate four densities, etc.).

It is also understood that the emulator of the present subject matter can comprise a layered material of alternating non-conductive dielectric layers and lossy or conductive layers. Alternating layers of dielectric materials will show the Maxwell Wagner effect which is a frequency dependent response. This is similar to the Maxwell Wagner effects experienced with moist aggregates. It is further envisioned that the non-conductive dielectric layer in an emulator of the present subject matter can comprise holes in order to let gases and/or conducting liquids circulate in order to change the dielectric constants of the emulator. It is further envisioned that the non-conductive dielectric layer in an emulator of the present subject matter can comprise holes in order to let gases and/or conducting liquids circulate in order to change the dielectric constants of the emulator.

Figure 14:
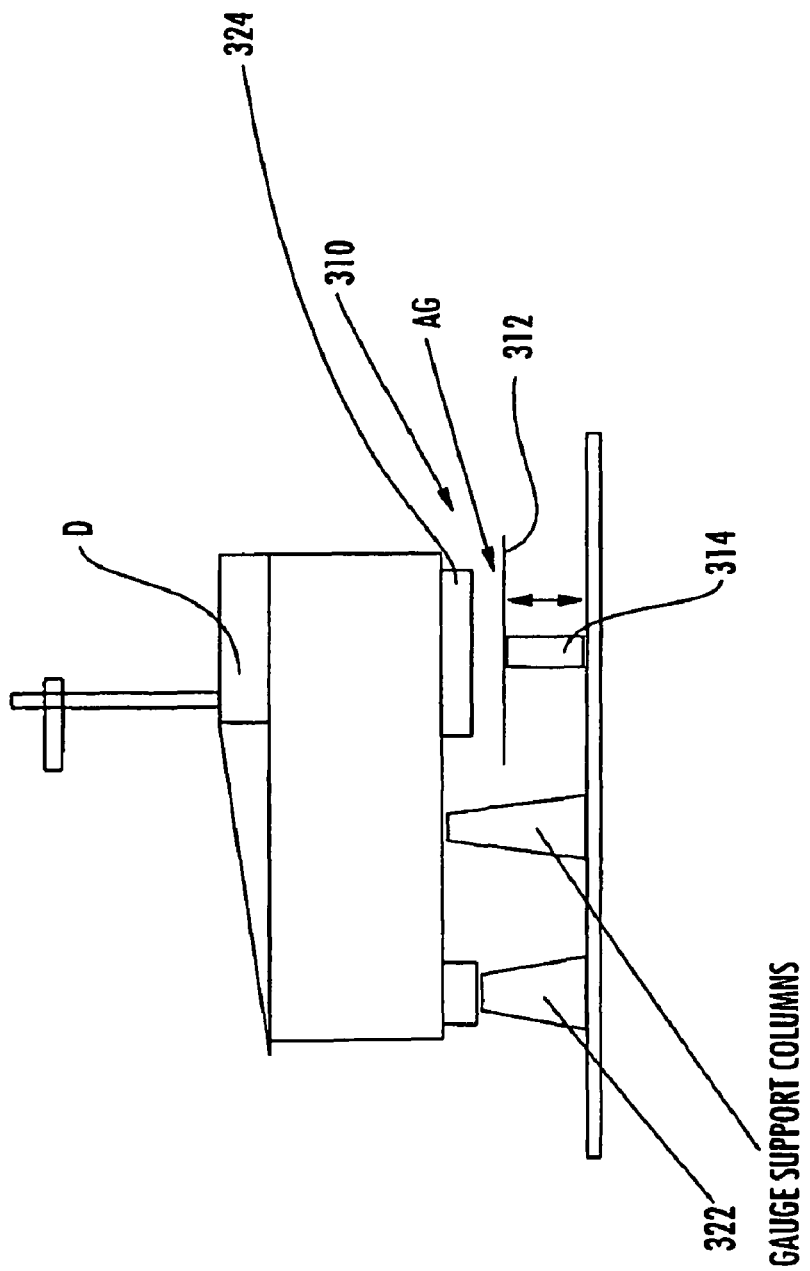
FIG. 14 is a side profile view of a reference emulator comprising a mechanically adjustable conducting plate in accordance with an embodiment of the present subject matter.

Additionally, and with reference to FIG. 14, one embodiment of the emulator of the present subject matter can comprise mechanically moving or mechanically adjustable non-conductive or conductive materials in order to mimic various dielectric constants. For example, as shown in FIG. 14, a mechanical emulator 310 can comprise an adjustable conducting plate 312 on a moveable piston 314. In this embodiment, an electromagnetic gauge device D with a sensor 324 sits on one or more support columns 322. An air gap AG between sensor 324 and conducting plate 312 acts as the dielectric of the system and as a hand crank or motor is turned and piston 314 moves upwardly, conducting plate 312 gets closer to the sensor 324 of device D. As such, the energy stored in the dielectric is changed and the effective dielectric constant of the system is changed. Conducting plate 312 can be brought toward and away from sensor 324 to simulate various dielectric constants for calibration. Instead of an air gap, it is envisioned that, as described above, the dielectric can be any other suitable non-conductive material (such as plastic) and the mechanical system can involve the moving of a conductive plate towards and away from the dielectric to produce different effective dielectric constants.

Artificial Dielectric Cores

An asphalt plant periodically tests the produced asphalt material to verify that the product meets engineering specifications. Often, electromagnetic gauges are used to test asphalt in the field (e.g., after being laid) to obtain this confirmation. These gauges usually must be field off-set from original factory calibration in order to account for varying field conditions. Since electromagnetic gauges read dielectric constants and map (relate) this to density, there are two typical methods used to convert gauge readings to true density values. These methods assume that the gauge reading (R) and the true reading (T) have a linear relationship given by T=m*R+b where m and b are the slope and the intercept.

In the first method, field data is used to determine a constant to adjust the intercept b. Gauge readings are taken on one or more (preferably three) locations in the middle of an asphalt lane. Cores are then extracted from these locations and the true density values are determined. The gauge and core density readings for the preferable three locations are classified as (G1, C1), (G2, C2), and (G3, C3). The density difference for the locations are D1, D2, and D3 calculated by D1=G1−C1, D2=G2−C2, and D3=G3−C3. The average density difference is DA calculated by DA=(D1+D2+D3)/3. The value of DA can then be entered into the gauge and thereafter the gauge adds the value DA for all readings given by T=R+b+DA.

In the second method, field data is used to determine a project mix specific slope (m') and intercept (b'). Gauge readings are taken on two or more spots in the middle of an asphalt lane as well as close to the edge of the lane. The method further requires extraction and determination of actual density of cores from the gauge reading locations for the off-set calculation.

Both of these methods require the extraction and determination of actual density of core samples from the asphalt lane, which is both labor and time intensive. As such, many asphalt plants produce cylindrical test specimens using gyratory compactors (known as "pills" or "pucks"). These specimens can be made to have different compaction levels and can be used to determine the mix specific calibration, thereby eliminating the need for core extraction from the pavement and time delays for obtaining true density values. For example, consider that three cylindrical specimens are made by a gyratory compactor having three density values. If gauge readings are taken on the specimens as G1, G2, and G3 and true density values on the specimens are determined to be C1, C2, and C3, then the adjustment to b or a new set of m and b values with a finite element correction can be calculated using the calculations of the first or second method discussed above (without the need for destructive asphalt cores). Alternatively, a second instrument could be used to obtain the dielectric constant of the cores vs. density, and this can be mapped to the field instrument. The second instrument can be a broadband cell that measures the bulk electrical properties of the core (throughout the volume of material). The density can also be obtained using a dry method such as laser scanning or nuclear analysis such as the TROXLER COREREADER™.

A gyratory compactor can be used to make laboratory test specimens from the field mix materials, such as asphalt and soil with different moisture contents. Using the gyro, the method of calibration would be to make a set of specimens that have a low, medium and high density as a function of moisture. The dielectric response of these samples could then be measured as a function of density, based on moisture over a wide frequency band. This data could be mapped to field instruments for field portable sensors, thereby reducing further field analysis. This method could aid in correction for specific job site variables such as the binder type, mineralogy of the mix, aggregate texture, orientation, and size. Another method of calibration would be to measure the specimen pucks directly with the field instrument in the lab. For example, the field instrument could be positioned directly on the specimen and a measurement obtained as a function of density. The field instrument could use its own computational efforts to obtain the calibration curve specific to that material.

In light of the above, there is a long-felt need for the ability to produce test specimen pucks so that destructive core sampling is not required. It is also desired that these test specimens be able to be produced with known dielectric constants that would emulate dielectric constants of a known material, such as field mix (asphalt material).

As discussed above, artificial dielectrics are basically large-scale models of a dipolar molecule, constructed by arranging conductors in a 3-D pattern. A lightweight binder or filler material such as polystyrene supports the conductors. The result is a manmade material that simulates an ordinary dielectric material with a dipole moment. The combined effect of all the individual conductors of the lattice is to produce a net dipole polarization P per unit volume.

The present subject matter contemplates an artificial dielectric for emulating the dielectric constant of a material, such as for the production of a test specimen puck. The artificial dielectric typically comprises a substrate matrix having a dielectric constant less than the material dielectric constant and an additive combined with the substrate, the additive having a dielectric constant higher than the material dielectric constant. The substrate can be a material such as polystyrene or epoxy and can contain voids defining a gas such as air. The additive can consist of conductive metal particles such as metal strips, disks, needles, spheres, ellipsoids, and cylinders, or a high dielectric powder such as barium titanate, titanium dioxide, and boron nitride.

Figure 15:
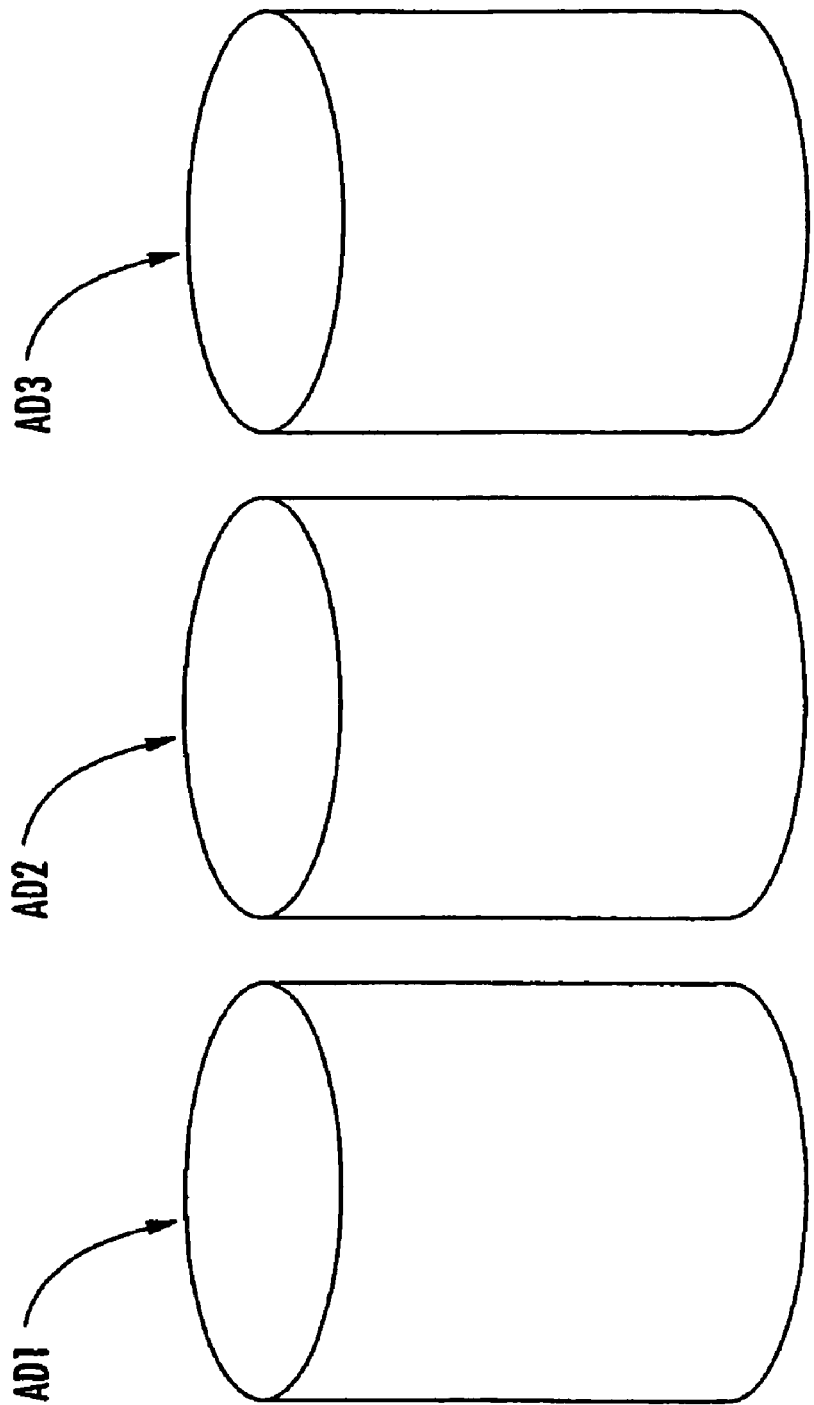
FIG. 15 is a perspective view of a plurality of artificial dielectric specimens for calibration of electromagnetic gauges in accordance with an embodiment of the present subject matter.

Referring to FIG. 15, it is envisioned that a plurality of artificial dielectric specimens (three shown generally as AD1, AD2, AD3 in FIG. 15) could be produced wherein dielectric AD1 has a density D1, dielectric AD2 has a different density D2, and dielectric AD3 has a different density D3. These specimens of varying densities could be used for gauge calibration as described hereinabove. While the test specimen artificial dielectric is preferably in a cylindrical "puck" shape (see FIG. 15), it is understood that the specimen can be a rectangular slab, circular, triangular, or other suitable shape.

REFERENCES

The references listed below are incorporated herein by reference to the extent that they supplement, explain, provide a background for or teach methodology, techniques and/or processes employed herein. All cited patent documents and publications referred to in this application are herein expressly incorporated by reference.

W. E. Kock, "Metallic Delay Lines," *Bell System Technical Journal*, vol. 27, pp. 58-82 (1948);

G. S. Smith and W. R. Scott, Jr., "Antennas and Propagation Society International Symposium, 1988," *AP-S Digest*, pp. 594 and 596 (Jun. 6-10, 1988);

G. S. Smith and W. R. Scott, Jr., "The Use of Emulsions to Represent Dielectric Materials in Electromagnetic Scale Models," *IEEE Transactions on Antennas and Propagation*, vol. 38, no. 3 (March 1990);

Robert E. Collin, "Field Theory of Guided Waves," Second Edition, IEEE Press (1991);

ASTM D 7113-05, "Standard Test Method for Density of Bituminous Paving Mixtures in Place by the Electromagnetic Surface Contact Methods," ASTM International (2005);

U.S. Pat. No. 5,801,537 for METHOD AND APPARATUS FOR MEASURING IN-PLACE SOIL DENSITY AND MOISTURE CONTENT to Siddiqui et al.;

U.S. Pat. No. 5,900,736 for PAVING MATERIAL DENSITY INDICATOR AND METHOD USING CAPACITANCE to Sovik et al.;

U.S. Pat. No. 5,933,015 for METHOD AND APPARATUS FOR MEASURING IN-PLACE SOIL DENSITY AND MOISTURE CONTENT to Siddiqui et al.;

U.S. Pat. No. 6,215,317 for METHOD AND APPARATUS FOR MEASURING IN-PLACE DENSITY AND MOISTURE CONTENT to Siddiqui et al.;

U.S. Pat. No. 6,369,381 for APPARATUS AND METHOD FOR CALIBRATION OF NUCLEAR GAUGES to Troxler et al.;

U.S. Pat. No. 6,388,453 for SWEPT-FREQUENCY DIELECTRIC MOISTURE AND DENSITY SENSOR to Greer;

U.S. Pat. No. 6,400,161 for MATERIAL SEGREGATION AND DENSITY ANALYZING APPARATUS AND METHOD to Geisel;

U.S. Pat. No. 6,414,497 for PAVING MATERIAL ANALYZER SYSTEM AND METHOD to Sovik et al.;

U.S. Pat. No. 6,677,763 for MATERIAL SEGREGATION, DENSITY, AND MOISTURE ANALYZING APPARATUS AND METHOD to Geisel;

U.S. Pat. No. 6,803,771 for PAVING MATERIAL ANALYZER SYSTEM AND METHOD to Sovik et al.;

U.S. Patent Application Publication No. 2004/0095154 for ELECTRICALLY MEASURING SOIL DENSITY AND SOIL MOISTURE CONTENT to Lundstrom et al.; and U.S. Patent Application Publication No. 2005/0150278 for PAVEMENT MATERIAL MICROWAVE DENSITY MEASUREMENT METHODS AND APPARATUSES to Troxier et al.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A system for calibration of a dielectric sensitive probe to account for changes in gauge geometry and other factors affecting gauge calibration accuracy, the system comprising:
(a) a plurality of emulator apparatuses for emulating electrical characteristics of a plurality of materials having different known dielectric constants, wherein each emulator apparatus is associated with one of the plurality of materials and further wherein each emulator apparatus comprises an electrically simulated layer having a dielectric properties representing the associated one material dielectric constant;
wherein the dielectric sensitive probe is used for the measurement of material selected from the group consisting of soil, sand, aggregate, asphalt, cement, and composites thereof.

2. The system for calibration of a dielectric sensitive probe according to claim 1 wherein the electrically simulated layer of each emulator apparatus is a plate constructed of material selected from the group consisting of fiberglass, plastics, ceramics, polymers, glass, and composites thereof.

3. The system for calibration of a dielectric sensitive probe according to claim 1 wherein the electrically simulated layer of each emulator apparatus is a laminate constructed with a thickness in the range of about 0.375 to 6.000 inches.

4. The system for calibration of a dielectric sensitive probe according to claim 1 wherein each emulator apparatus further comprises an absorbent lossy layer positioned below the electrically simulated layer.

5. The system for calibration of a dielectric sensitive probe according to claim 1 wherein the system is used with a dielectric sensitive probe having electrodes mounted for sensing a dielectric constant adjacent to the probe.

6. The system for calibration of a dielectric sensitive probe according to claim 5 wherein the dielectric sensitive probe is used for the measurement of material selected from the group consisting of soil, sand, aggregate, asphalt, cement, and composites thereof.

7. A system for calibration of a dielectric sensitive probe to account for changes in gauge geometry and other factors affecting gauge calibration accuracy, the system comprising:
  (a) a first emulator apparatus for emulating electrical characteristics of a first material having a known dielectric constant, the first emulator apparatus comprising:
    an electrically simulated layer having a dielectric constant approximate the first material dielectric constant; and
  (b) a second emulator apparatus for emulating electrical characteristics of a second material having a known dielectric constant different from the dielectric constant of the first material, the second emulator apparatus comprising:
    (i) an electrically simulated layer having a dielectric constant of about the second material dielectric constant; and
  (c) a third emulator apparatus for emulating electrical characteristics of a third material having a known dielectric constant different from the dielectric constants of the first and second materials, the third emulator apparatus comprising:
    (i) an electrically simulated layer having a dielectric constant of about the third material dielectric constant; and
  wherein the electrically simulated layer represents pavement materials of one of the groups of soil, sand, aggregate, asphalt, cement, and composites thereof.

8. The system for calibration of a dielectric sensitive probe according to claim 7 wherein the electrically simulated layer of each of the first, second, and third emulator apparatuses is a surface constructed of material selected from the group consisting of fiberglass, plastics, ceramics, polymers, glass, and composites thereof.

9. The system for calibration of a dielectric sensitive probe according to claim 7 wherein the electrically simulated layer of each of the first, second, and third emulator apparatuses is a surface constructed of an electrically simulated layer with a thickness in the range of about 0.375 to 6.000 inches.

10. The system for calibration of a dielectric sensitive probe according to claim 7 wherein each of the first, second, and third emulator apparatuses further comprises an absorbent lossy layer positioned below the electrically simulated layer.

11. The system for calibration of a dielectric sensitive probe according to claim 7 wherein the system is used with a dielectric sensitive probe having electrodes mounted for sensing a dielectric constant adjacent to the probe.

12. The system for calibration of a dielectric sensitive probe according to claim 11 wherein the dielectric sensitive probe is used for the measurement of material selected from the group consisting of soil, sand, aggregate, asphalt, cement, and composites thereof.

13. An emulator apparatus for emulating electrical characteristics of a material having a known dielectric constant, the emulator apparatus comprising:
  (a) a first electrically non-conductive layer having a dielectric constant approximately equal to the material dielectric constant;
  (b) at least one second electrically non-conductive layer having a dielectric constant greater than or equal to 1.0, the at least one second electrically non-conductive layer adjacent the first non-conductive layer; and
  (c) a dielectric sensitive probe used for the measurement of material selected from the group consisting of soil, sand, aggregate, asphalt, cement, and composites thereof.

14. A combination carrying case and emulator apparatus comprising:
  (a) a housing adapted for containing a dielectric sensitive probe, the housing having a base and a cover; and
  (b) an emulator apparatus disposed within the housing for emulating electrical characteristics of a material having a known dielectric constant, the emulator apparatus comprising:
    i. a first electrically non-conductive layer having a dielectric constant approximately equal to the material dielectric constant; and
    ii. at least one second electrically non-conductive layer having a dielectric constant greater than or equal to 1.0, the at least one second non-conductive layer adjacent the first non-conductive layer;
  wheras the electrically non-conductive layers are selected to have properties including the frequency response of the group consisting of soil, sand, aggregate, asphalt, cement, and composites thereof.

* * * * *